US007232671B2

(12) United States Patent
Cieplak

(10) Patent No.: US 7,232,671 B2
(45) Date of Patent: Jun. 19, 2007

(54) PERTUSSIS TOXIN GENE: CLONING AND EXPRESSION OF PROTECTIVE ANTIGEN

(75) Inventor: Witold Cieplak, Poulsbo, WA (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 379 days.

(21) Appl. No.: 10/744,731

(22) Filed: Dec. 23, 2003

(65) Prior Publication Data

US 2006/0159710 A1 Jul. 20, 2006

Related U.S. Application Data

(63) Continuation of application No. 09/792,861, filed on Feb. 23, 2001, now abandoned, which is a continuation of application No. 08/483,326, filed on Jun. 7, 1995, now abandoned, which is a continuation of application No. 07/542,149, filed on Jun. 22, 1990, which is a continuation of application No. 07/311, 612, filed on Feb. 15, 1989, now abandoned.

(51) Int. Cl.
*C12N 9/00* (2006.01)

(52) U.S. Cl. ...................................................... 435/183

(58) Field of Classification Search ................. 435/183
See application file for complete search history.

(56) References Cited

U.S. PATENT DOCUMENTS 4,883,761 A 11/1989 Keith et al. .............. 435/320.1
5,085,862 A 2/1992 Klein et al. ................... 424/92
5,244,657 A * 9/1993 Klein et al. ................. 435/193
5,773,600 A * 6/1998 Burnette, III .............. 536/23.7
6,713,072 B1 * 3/2004 Pizza et al. .............. 424/240.1

OTHER PUBLICATIONS

Burnette et al. Oct. 7, 1988. Pertussis toxin S1 mutant with reduced enzyme activity and a conserved protective epitope. Science vol. 242, pp. 72-74.*

Sekura et al., *J. Biol. Chem.*, vol. 258:14647-14651, (1983).

Katada et al., *Arch. Biochem. Biophys.*, vol. 224:290-298, (1983).

Weiss et al., *Infec. and Immun.*, vol. 42:33-41, (1983).

Hunkappiler et al., *Meth. Enzymol.*, vol. 91:399-413, (1983).

Beaucage et al., *Tetrahedron Letters*, vol. 22:1859-1862, (1981).

Wallace et al., *Nuc. Acids Res.*, vol. 9:879-894, (1981).

Locht et al., *Science*, vol. 232:1258-1264, (1986).

Nicosia et al., *Proc. Natl. Acad. Sci. USA*, vol. 83:4631-4635, (1986).

Cantor et al., *biophysical Chenmistry*, Part I The Conformation of Biological Macromolecules. W. H. Freeman and Col., San Francisco, pp. 3-39, (1980).

Burnetter et al., *J. Cell. Biochem. Suppl.*, 128, 4, (1988).

Pizza et al., *Proc. Nat'l. Acad. Sci. USA*, vol. 85:7521-7525, (1988).

* cited by examiner

*Primary Examiner*—Karen Cochrane Carlson
(74) *Attorney, Agent, or Firm*—Morgan & Finnegan LLP

(57) ABSTRACT

A cloned gene encoding the expression of an antigenic mutant pertussis toxin with substantially reduced enzymatic activity has been described.

1 Claim, 5 Drawing Sheets

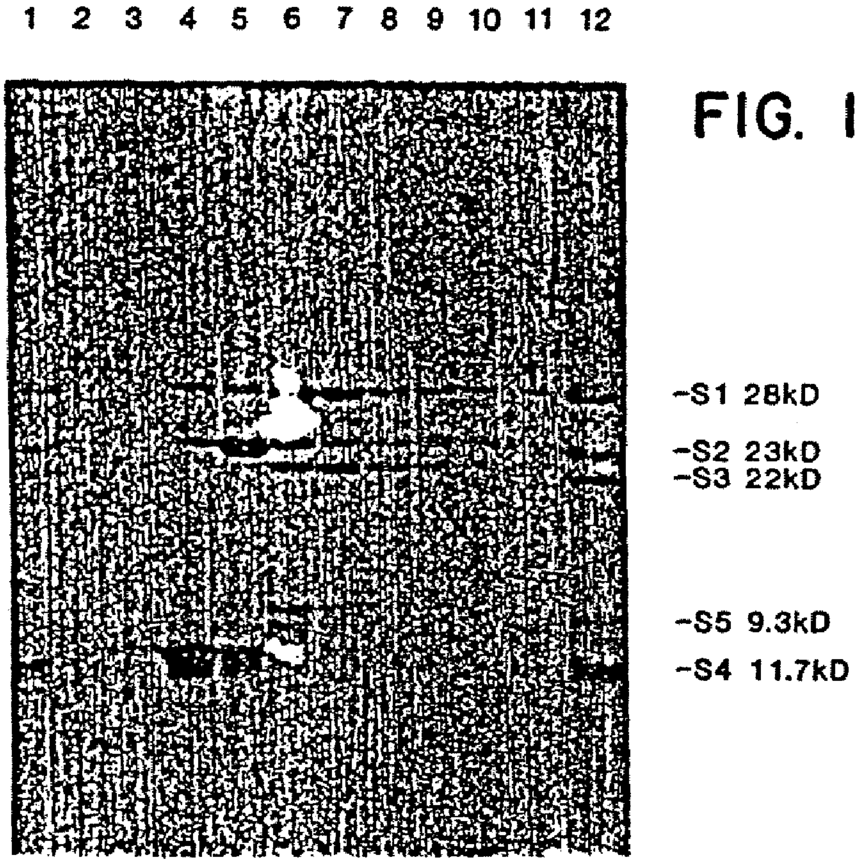
FIG. 1
FIG. 3a
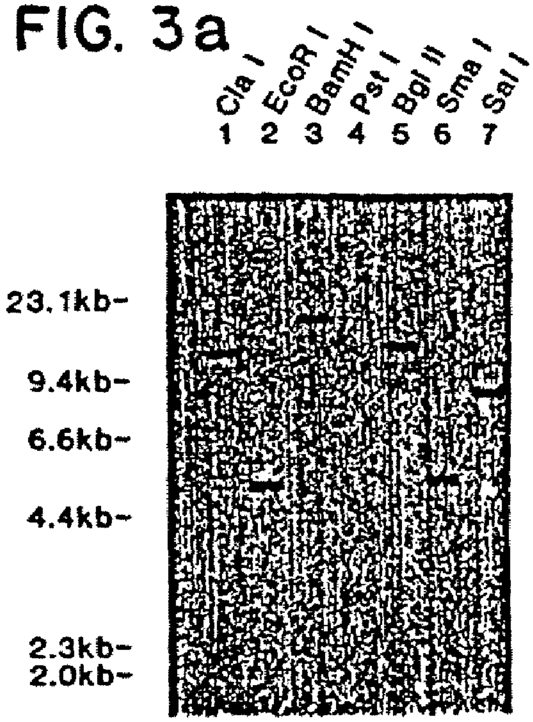
FIG. 3b
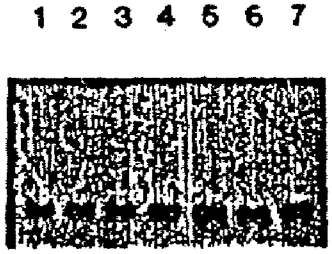
FIG. 3c
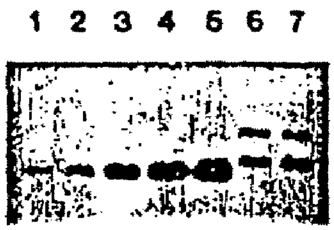

SEQUENCE LISTING

<160> NUMBER OF SEQ ID NOS: 28

<210> SEQ ID NO 1
<211> LENGTH: 184
<212> TYPE: DNA
<213> ORGANISM: Bordetella pertussis

<400> SEQUENCE: 1
cccgggacag ggcggcgccc ggcggtcgcg ggtccgcgcc ctggcgtggt tcctgccatc 60
cggcgcgatg acgcatcttt cccccgccct ggccgacgtt ccttatgtgc tggtgaagac 120

-continued

```
caatatggtg gtcaccagcg tagccatgaa gccgtatgaa gtcaccccga cgcggatgct    180

ggtc                                                                 184


<210> SEQ ID NO 2
<211> LENGTH: 61
<212> TYPE: PRT
<213> ORGANISM: Bordetella pertussis

<400> SEQUENCE: 2

Pro Gly Gln Gly Gly Ala Arg Arg Ser Arg Val Arg Ala Leu Ala Trp
  1               5                  10                  15

Leu Leu Ala Ser Gly Ala Met Thr His Leu Ser Pro Ala Leu Ala Asp
             20                  25                  30

Val Pro Tyr Val Leu Val Lys Thr Asn Met Val Val Thr Ser Val Ala
         35                  40                  45

Met Lys Pro Tyr Glu Val Thr Pro Thr Arg Met Leu Val
     50                  55                  60


<210> SEQ ID NO 3
<211> LENGTH: 17
<212> TYPE: DNA
<213> ORGANISM: Bordetella pertussis
<220> FEATURE:
<223> OTHER INFORMATION: Purine (P) R=G or A; Y=T or C; N=A, C, G, or T
<220> FEATURE:
<221> NAME/KEY: modified_base
<222> LOCATION: (6)
<220> FEATURE:
<221> NAME/KEY: modified_base
<222> LOCATION: (9)
<220> FEATURE:
<221> NAME/KEY: modified_base
<222> LOCATION: (12)
<220> FEATURE:
<221> NAME/KEY: modified_base
<222> LOCATION: (15)

<400> SEQUENCE: 3

atgaarccnt aygargt                                                    17


<210> SEQ ID NO 4
<211> LENGTH: 30
<212> TYPE: PRT
<213> ORGANISM: Bordetella pertussis
<220> FEATURE:
<223> OTHER INFORMATION: Xaa = Any amino acid; the 8th Val and 4th Pro
      are questionable.
<220> FEATURE:
<221> NAME/KEY: VARIANT
<222> LOCATION: (15)

<400> SEQUENCE: 4

Asp Val Pro Tyr Val Leu Val Lys Thr Asn Met Val Val Thr Xaa Val
  1               5                  10                  15

Ala Met Lys Pro Tyr Glu Val Val Pro Pro Arg Met Leu Val
             20                  25                  30


<210> SEQ ID NO 5
<211> LENGTH: 4210
<212> TYPE: DNA
<213> ORGANISM: Bordetella pertussis
<220> FEATURE:
<221> NAME/KEY: CDS
<222> LOCATION: (609)..(1310)
<220> FEATURE:
<221> NAME/KEY: CDS
<222> LOCATION: (1434)..(2030)
```

-continued

```
<220> FEATURE:
<221> NAME/KEY: CDS
<222> LOCATION: (2153)..(2482)
<220> FEATURE:
<221> NAME/KEY: CDS
<222> LOCATION: (2557)..(2856)
<220> FEATURE:
<221> NAME/KEY: CDS
<222> LOCATION: (3026)..(3622)

<400> SEQUENCE: 5

gaattcgtcg cctcgccctg gttcgccgtc atggccccca agggaaccga ccccaagata     60

atcgtcctgc tcaaccgcca catcaacgag gcgctgcagt ccaaggcggt cgtcgaggcc    120

tttgccgccc aaggcgccac gccggtcatc gccacgccgg atcagacccg cggcttcatc    180

gcagacgaga tccagcgctg ggccggcgtc gtgcgcgaaa ccggcgccaa gctgaagtag    240

cagcgcagcc ctccaacgcg ccatccccgt ccggccggca ccatcccgca tacgtgttgg    300

caaccgccaa cgcgcatgcg tgcagattcg tcgtacaaaa ccctcgattc ttccgtacat    360

cccgctactg caatccaaca cggcatgaac gctccttcgg cgcaaagtcg cgcgatggta    420

ccggtcaccg tccggaccgt gctgaccccc ctgccatggt gtgatcccta aaataggcac    480

catcaaaacg cagaggggaa gacgggatgc gttgcactcg ggcaattcgc caaaccgcaa    540

gaacaggctg gctgacgtgg ctggcgattc ttgccgtcac ggcgcccgtg acttcgccgg    600

catgggcc gac gat cct ccc gcc acc gta tac cgc tat gac tcc cgc ccg     650
         Asp Asp Pro Pro Ala Thr Val Tyr Arg Tyr Asp Ser Arg Pro
           1               5                  10

ccg gag gac gtt ttc cag aac gga ttc acg gcg tgg gga aac aac gac      698
Pro Glu Asp Val Phe Gln Asn Gly Phe Thr Ala Trp Gly Asn Asn Asp
 15                  20                  25                  30

aat gtg ctc gac cat ctg acc gga cgt tcc tgc cag gtc ggc agc agc      746
Asn Val Leu Asp His Leu Thr Gly Arg Ser Cys Gln Val Gly Ser Ser
                 35                  40                  45

aac agc gct ttc gtc tcc acc agc agc agc cgg cgc tat acc gag gtc      794
Asn Ser Ala Phe Val Ser Thr Ser Ser Ser Arg Arg Tyr Thr Glu Val
             50                  55                  60

tat ctc gaa cat cgc atg cag gaa gcg gtc gag gcc gaa cgc gcc ggc      842
Tyr Leu Glu His Arg Met Gln Glu Ala Val Glu Ala Glu Arg Ala Gly
         65                  70                  75

agg ggc acc ggc cac ttc atc ggc tac atc tac gaa gtc cgc gcc gac      890
Arg Gly Thr Gly His Phe Ile Gly Tyr Ile Tyr Glu Val Arg Ala Asp
     80                  85                  90

aac aat ttc tac ggc gcc gcc agc tcg tac ttc gaa tac gtc gac act      938
Asn Asn Phe Tyr Gly Ala Ala Ser Ser Tyr Phe Glu Tyr Val Asp Thr
 95                 100                 105                 110

tat ggc gac aat gcc ggc cgt atc ctc gcc ggc gcg ctg gcc acc tac      986
Tyr Gly Asp Asn Ala Gly Arg Ile Leu Ala Gly Ala Leu Ala Thr Tyr
                115                 120                 125

cag agc gaa tat ctg gca cac cgg cgc att ccg ccc gaa aac atc cgc     1034
Gln Ser Glu Tyr Leu Ala His Arg Arg Ile Pro Pro Glu Asn Ile Arg
            130                 135                 140

agg gta acg cgg gtc tat cac aac ggc atc acc ggc gag acc acg acc     1082
Arg Val Thr Arg Val Tyr His Asn Gly Ile Thr Gly Glu Thr Thr Thr
        145                 150                 155

acg gag tat tcc aac gct cgc tac gtc agc cag cat act cgc gcc aat     1130
Thr Glu Tyr Ser Asn Ala Arg Tyr Val Ser Gln His Thr Arg Ala Asn
    160                 165                 170

ccc aac ccc tac aca tcg cga agg tcc gta gcg tcg atc gtc ggc aca     1178
Pro Asn Pro Tyr Thr Ser Arg Arg Ser Val Ala Ser Ile Val Gly Thr
175                 180                 185                 190
```

-continued

```
ttg gtg cgc atg gcg ccg gtg ata ggc gct tgc atg gcg cgg cag gcc      1226
Leu Val Arg Met Ala Pro Val Ile Gly Ala Cys Met Ala Arg Gln Ala
                195                 200                 205

gaa agc tcc gag gcc atg gca gcc tgg tcc gaa cgc gcc ggc gag gcg      1274
Glu Ser Ser Glu Ala Met Ala Ala Trp Ser Glu Arg Ala Gly Glu Ala
            210                 215                 220

atg gtt ctc gtg tac tac gaa agc atc gcg tat tcg ttctagacct           1320
Met Val Leu Val Tyr Tyr Glu Ser Ile Ala Tyr Ser
        225                 230

ggcccagccc cgcccaactc cggtaattca acagcatgcc gatcgaccgc aagacgctct   1380

gccatctcct gtccgttctg ccgttggccc tcctcggatc tcacgtggcg cgg gcc      1436
                                                           Ala
                                                           235

tcc acg cca ggc atc gtc att ccg ccg cag gaa cag att acc cag cat      1484
Ser Thr Pro Gly Ile Val Ile Pro Pro Gln Glu Gln Ile Thr Gln His
                240                 245                 250

ggc agc ccc tat gga cgc tgc gcg aac aag acc cgt gcc ctg acc gtg      1532
Gly Ser Pro Tyr Gly Arg Cys Ala Asn Lys Thr Arg Ala Leu Thr Val
            255                 260                 265

gcg gaa ttg cgc ggc agc ggc gat ctg cag gag tac ctg cgt cat gtg      1580
Ala Glu Leu Arg Gly Ser Gly Asp Leu Gln Glu Tyr Leu Arg His Val
        270                 275                 280

acg cgc ggc tgg tca ata ttt gcg ctc tac gat ggc acc tat ctc ggc      1628
Thr Arg Gly Trp Ser Ile Phe Ala Leu Tyr Asp Gly Thr Tyr Leu Gly
    285                 290                 295

ggc gaa tat ggc ggc gtg atc aag gac gga aca ccc ggc ggc gca ttc      1676
Gly Glu Tyr Gly Gly Val Ile Lys Asp Gly Thr Pro Gly Gly Ala Phe
300                 305                 310                 315

gac ctg aaa acg acg ttc tgc atc atg acc acg cgc aat acg ggt caa      1724
Asp Leu Lys Thr Thr Phe Cys Ile Met Thr Thr Arg Asn Thr Gly Gln
                320                 325                 330

ccc gca acg gat cac tac tac agc aac gtc acc gcc act cgc ctg ctc      1772
Pro Ala Thr Asp His Tyr Tyr Ser Asn Val Thr Ala Thr Arg Leu Leu
            335                 340                 345

tcc agc acc aac agc agg cta tgc gcg gtc ttc gtc aga agc ggg caa      1820
Ser Ser Thr Asn Ser Arg Leu Cys Ala Val Phe Val Arg Ser Gly Gln
        350                 355                 360

ccg gtc att ggc gcc tgc acc agc ccg tat gac ggc aag tac tgg agc      1868
Pro Val Ile Gly Ala Cys Thr Ser Pro Tyr Asp Gly Lys Tyr Trp Ser
    365                 370                 375

atg tac agc cgg ctg cgg aaa atg ctt tac ctg atc tac gtg gcc ggc      1916
Met Tyr Ser Arg Leu Arg Lys Met Leu Tyr Leu Ile Tyr Val Ala Gly
380                 385                 390                 395

atc tcc gta cgc gtc cat gtc agc aag gaa gaa cag tat tac gac tat      1964
Ile Ser Val Arg Val His Val Ser Lys Glu Glu Gln Tyr Tyr Asp Tyr
                400                 405                 410

gag gac gca acg ttc gag act tac gcc ctt acc ggc atc tcc atc tgc      2012
Glu Asp Ala Thr Phe Glu Thr Tyr Ala Leu Thr Gly Ile Ser Ile Cys
            415                 420                 425

aat cct gga tca tcc tta tgctgagacg cttccccact cgaaccaccg            2060
Asn Pro Gly Ser Ser Leu
        430

ccccgggaca gggcggcgcc cggcggtcgc gcatgcgcgc cctggcgtgg ttgctggcat   2120

ccggcgcgat gacgcatctt tcccccgccc tg gcc gac gtt cct tat gtg ctg      2173
                                    Ala Asp Val Pro Tyr Val Leu
                                        435                 440

gtg aag acc aat atg gtg gtc acc agc gta gcc atg aag ccg tat gaa      2221
Val Lys Thr Asn Met Val Val Thr Ser Val Ala Met Lys Pro Tyr Glu
```

-continued

```
            445                 450                 455

gtc acc ccg acg cgc atg ctg gtc tgc ggc atc gcc gcc aaa ctg ggc     2269
Val Thr Pro Thr Arg Met Leu Val Cys Gly Ile Ala Ala Lys Leu Gly
            460                 465                 470

gcc gcg gcc agc agc ccg gac gcg cac gtg ccg ttc tgc ttc ggc aag     2317
Ala Ala Ala Ser Ser Pro Asp Ala His Val Pro Phe Cys Phe Gly Lys
        475                 480                 485

gat ctc aag cgt ccc ggc agc agt ccc atg gaa gtc atg ttg cgc gcc     2365
Asp Leu Lys Arg Pro Gly Ser Ser Pro Met Glu Val Met Leu Arg Ala
    490                 495                 500

gtc ttc atg caa caa cgg ccg ctg cgc atg ttt ctg ggt ccc aag caa     2413
Val Phe Met Gln Gln Arg Pro Leu Arg Met Phe Leu Gly Pro Lys Gln
505                 510                 515                 520

ctc act ttc gaa ggc aag ccc gcg ctc gaa ctg atc cgg atg gtc gaa     2461
Leu Thr Phe Glu Gly Lys Pro Ala Leu Glu Leu Ile Arg Met Val Glu
                525                 530                 535

tgc agc ggc aag cag gat tgc ccctgaaggc gaaccccatg cataccatcg        2512
Cys Ser Gly Lys Gln Asp Cys
            540

catccatcct gttgtccgtg ctcggcatat acagcccggc tgac gtc gcc ggc ttg    2568
                                                 Val Ala Gly Leu
                                                     545

ccg acc cat ctg tac aag aac ttc act gtc cag gag ctg gcc ttg aaa     2616
Pro Thr His Leu Tyr Lys Asn Phe Thr Val Gln Glu Leu Ala Leu Lys
        550                 555                 560

ctg aag ggc aag aat cag gag ttc tgc ctg acc gcc ttc atg tcg ggc     2664
Leu Lys Gly Lys Asn Gln Glu Phe Cys Leu Thr Ala Phe Met Ser Gly
    565                 570                 575

aga agc ctg gtc cgg gcg tgc ctg tcc gac gcg gga cac gag cac gac     2712
Arg Ser Leu Val Arg Ala Cys Leu Ser Asp Ala Gly His Glu His Asp
580                 585                 590                 595

acg tgg ttc gac acc atg ctt ggc ttt gcc ata tcc gcg tat gcg ctc     2760
Thr Trp Phe Asp Thr Met Leu Gly Phe Ala Ile Ser Ala Tyr Ala Leu
                600                 605                 610

aag agc cgg atc gcg ctg acg gtg gaa gac tcg ccg tat ccg ggc act     2808
Lys Ser Arg Ile Ala Leu Thr Val Glu Asp Ser Pro Tyr Pro Gly Thr
            615                 620                 625

ccc ggc gat ctg ctc gaa ctg cag atc tgc ccg ctc aac gga tat tgc     2856
Pro Gly Asp Leu Leu Glu Leu Gln Ile Cys Pro Leu Asn Gly Tyr Cys
        630                 635                 640

gaatgaaccc ttccggaggt ttcgacgttt ccgcgcaatc cgcttgagac gatcttccgc   2916

cctggttcca ttccgggaac accgcaacat gctgatcaac aacaagaagc tgcttcatca   2976

cattctgccc atcctggtgc tcgccctgct gggcatgcgc acggcccag gcc gtt gcg   3034
                                                      Ala Val Ala
                                                          645

cca ggc atc gtc atc ccg ccg aag gca ctg ttc acc caa cag ggc ggc     3082
Pro Gly Ile Val Ile Pro Pro Lys Ala Leu Phe Thr Gln Gln Gly Gly
            650                 655                 660

gcc tat gga cgc tgc ccg aac gga acc cgc gcc ttg acc gtg gcc gaa     3130
Ala Tyr Gly Arg Cys Pro Asn Gly Thr Arg Ala Leu Thr Val Ala Glu
        665                 670                 675

ctg cgc ggc aac gcc gaa ttg cag acg tat ttg cgc cag ata acg ccc     3178
Leu Arg Gly Asn Ala Glu Leu Gln Thr Tyr Leu Arg Gln Ile Thr Pro
    680                 685                 690

ggc tgg tcc ata tac ggt ctc tat gac ggt acg tac ctg ggc cag gcg     3226
Gly Trp Ser Ile Tyr Gly Leu Tyr Asp Gly Thr Tyr Leu Gly Gln Ala
695                 700                 705                 710

tac ggc ggc atc atc aag gac gcg ccg cca ggc gcg ggg ttc att tat     3274
```

-continued

```
Tyr Gly Gly Ile Ile Lys Asp Ala Pro Pro Gly Ala Gly Phe Ile Tyr
                715                 720                 725

cgc gaa act ttc tgc atc acg acc ata tac aag acc ggg caa ccg gct     3322
Arg Glu Thr Phe Cys Ile Thr Thr Ile Tyr Lys Thr Gly Gln Pro Ala
            730                 735                 740

gcg gat cac tac tac agc aag gtc acg gcc acg cgc ctg ctc gcc agc     3370
Ala Asp His Tyr Tyr Ser Lys Val Thr Ala Thr Arg Leu Leu Ala Ser
        745                 750                 755

acc aac agc agg ctg tgc gcg gta ttc gtc agg gac ggg caa tcg gtc     3418
Thr Asn Ser Arg Leu Cys Ala Val Phe Val Arg Asp Gly Gln Ser Val
    760                 765                 770

atc gga gcc tgc gcc agc ccg tat gaa ggc agg tac aga gac atg tac     3466
Ile Gly Ala Cys Ala Ser Pro Tyr Glu Gly Arg Tyr Arg Asp Met Tyr
775                 780                 785                 790

gac gcg ctg cgg cgc ctg ctg tac atg atc tat atg tcc ggc ctt gcc     3514
Asp Ala Leu Arg Arg Leu Leu Tyr Met Ile Tyr Met Ser Gly Leu Ala
                795                 800                 805

gta cgc gtc cac gtc agc aag gaa gag cag tat tac gac tac gag gac     3562
Val Arg Val His Val Ser Lys Glu Glu Gln Tyr Tyr Asp Tyr Glu Asp
            810                 815                 820

gcc aca ttc cag acc tat gcc ctc acc ggc att tcc ctc tgc aac ccg     3610
Ala Thr Phe Gln Thr Tyr Ala Leu Thr Gly Ile Ser Leu Cys Asn Pro
        825                 830                 835

gca gcg tcg ata tgctgagccg ccggctcgga tctgttcgcc tgtccatgtt         3662
Ala Ala Ser Ile
    840

tttccttgac ggataccgcg aatgaatccc ttgaaagact tgagagcatc gctaccgcgc   3722

ctggccttca tggcagcctg caccctgttg tccgccacgc tgcccgacct cgcccaggcc   3782

ggcggcgggc tgcagcgctg tcaaccactt catggcgacg atcgtggtcg tactgccgcg   3842

gcggtcagtg gccacggtga ccatcgccat aatctgggcg ggctacaagc tgctgttccg   3902

gcacgccgat gtgctggacg tggtgcgtgt ggtgctggcg ggagctgctg atcggcgcat   3962

cggccgaaat cgctcgttat ctgctgacct gaatcctgga cgtatcgaac atgcgtgatc   4022

cgcttttcaa gggctgcacc cggcgccgcg atgctgatgg cgtacccgcc acggcaggcc   4082

gtgtgcagcc ggcaccattc cctgctgggc catctcggtt cagcatccgc tttctggcct   4142

tgtttcccgt ggcattgctg gcgatgcgga tcatgatccg gcgcgatgac cagcagttcc   4202

gcctgatc                                                            4210


<210> SEQ ID NO 6
<211> LENGTH: 234
<212> TYPE: PRT
<213> ORGANISM: Bordetella pertussis

<400> SEQUENCE: 6

Asp Asp Pro Pro Ala Thr Val Tyr Arg Tyr Asp Ser Arg Pro Pro Glu
  1               5                  10                  15

Asp Val Phe Gln Asn Gly Phe Thr Ala Trp Gly Asn Asn Asp Asn Val
             20                  25                  30

Leu Asp His Leu Thr Gly Arg Ser Cys Gln Val Gly Ser Ser Asn Ser
         35                  40                  45

Ala Phe Val Ser Thr Ser Ser Ser Arg Arg Tyr Thr Glu Val Tyr Leu
     50                  55                  60

Glu His Arg Met Gln Glu Ala Val Glu Ala Glu Arg Ala Gly Arg Gly
 65                  70                  75                  80

Thr Gly His Phe Ile Gly Tyr Ile Tyr Glu Val Arg Ala Asp Asn Asn
```

-continued

```
                85                  90                  95

Phe Tyr Gly Ala Ala Ser Ser Tyr Phe Glu Tyr Val Asp Thr Tyr Gly
            100                 105                 110

Asp Asn Ala Gly Arg Ile Leu Ala Gly Ala Leu Ala Thr Tyr Gln Ser
        115                 120                 125

Glu Tyr Leu Ala His Arg Arg Ile Pro Pro Glu Asn Ile Arg Arg Val
    130                 135                 140

Thr Arg Val Tyr His Asn Gly Ile Thr Gly Glu Thr Thr Thr Thr Glu
145                 150                 155                 160

Tyr Ser Asn Ala Arg Tyr Val Ser Gln His Thr Arg Ala Asn Pro Asn
                165                 170                 175

Pro Tyr Thr Ser Arg Arg Ser Val Ala Ser Ile Val Gly Thr Leu Val
            180                 185                 190

Arg Met Ala Pro Val Ile Gly Ala Cys Met Ala Arg Gln Ala Glu Ser
        195                 200                 205

Ser Glu Ala Met Ala Ala Trp Ser Glu Arg Ala Gly Glu Ala Met Val
    210                 215                 220

Leu Val Tyr Tyr Glu Ser Ile Ala Tyr Ser
225                 230


<210> SEQ ID NO 7
<211> LENGTH: 199
<212> TYPE: PRT
<213> ORGANISM: Bordetella pertussis

<400> SEQUENCE: 7

Ala Ser Thr Pro Gly Ile Val Ile Pro Pro Gln Glu Gln Ile Thr Gln
  1               5                  10                  15

His Gly Ser Pro Tyr Gly Arg Cys Ala Asn Lys Thr Arg Ala Leu Thr
            20                  25                  30

Val Ala Glu Leu Arg Gly Ser Gly Asp Leu Gln Glu Tyr Leu Arg His
        35                  40                  45

Val Thr Arg Gly Trp Ser Ile Phe Ala Leu Tyr Asp Gly Thr Tyr Leu
    50                  55                  60

Gly Gly Glu Tyr Gly Gly Val Ile Lys Asp Gly Thr Pro Gly Gly Ala
65                  70                  75                  80

Phe Asp Leu Lys Thr Thr Phe Cys Ile Met Thr Thr Arg Asn Thr Gly
                85                  90                  95

Gln Pro Ala Thr Asp His Tyr Tyr Ser Asn Val Thr Ala Thr Arg Leu
            100                 105                 110

Leu Ser Ser Thr Asn Ser Arg Leu Cys Ala Val Phe Val Arg Ser Gly
        115                 120                 125

Gln Pro Val Ile Gly Ala Cys Thr Ser Pro Tyr Asp Gly Lys Tyr Trp
    130                 135                 140

Ser Met Tyr Ser Arg Leu Arg Lys Met Leu Tyr Leu Ile Tyr Val Ala
145                 150                 155                 160

Gly Ile Ser Val Arg Val His Val Ser Lys Glu Glu Gln Tyr Tyr Asp
                165                 170                 175

Tyr Glu Asp Ala Thr Phe Glu Thr Tyr Ala Leu Thr Gly Ile Ser Ile
            180                 185                 190

Cys Asn Pro Gly Ser Ser Leu
        195


<210> SEQ ID NO 8
<211> LENGTH: 110
```

-continued

<212> TYPE: PRT
<213> ORGANISM: Bordetella pertussis

<400> SEQUENCE: 8

```
Ala Asp Val Pro Tyr Val Leu Val Lys Thr Asn Met Val Val Thr Ser
  1               5                  10                  15

Val Ala Met Lys Pro Tyr Glu Val Thr Pro Thr Arg Met Leu Val Cys
             20                  25                  30

Gly Ile Ala Ala Lys Leu Gly Ala Ala Ala Ser Ser Pro Asp Ala His
         35                  40                  45

Val Pro Phe Cys Phe Gly Lys Asp Leu Lys Arg Pro Gly Ser Ser Pro
     50                  55                  60

Met Glu Val Met Leu Arg Ala Val Phe Met Gln Gln Arg Pro Leu Arg
 65                  70                  75                  80

Met Phe Leu Gly Pro Lys Gln Leu Thr Phe Glu Gly Lys Pro Ala Leu
                 85                  90                  95

Glu Leu Ile Arg Met Val Glu Cys Ser Gly Lys Gln Asp Cys
            100                 105                 110
```

<210> SEQ ID NO 9
<211> LENGTH: 100
<212> TYPE: PRT
<213> ORGANISM: Bordetella pertussis

<400> SEQUENCE: 9

```
Val Ala Gly Leu Pro Thr His Leu Tyr Lys Asn Phe Thr Val Gln Glu
  1               5                  10                  15

Leu Ala Leu Lys Leu Lys Gly Lys Asn Gln Glu Phe Cys Leu Thr Ala
             20                  25                  30

Phe Met Ser Gly Arg Ser Leu Val Arg Ala Cys Leu Ser Asp Ala Gly
         35                  40                  45

His Glu His Asp Thr Trp Phe Asp Thr Met Leu Gly Phe Ala Ile Ser
     50                  55                  60

Ala Tyr Ala Leu Lys Ser Arg Ile Ala Leu Thr Val Glu Asp Ser Pro
 65                  70                  75                  80

Tyr Pro Gly Thr Pro Gly Asp Leu Leu Glu Leu Gln Ile Cys Pro Leu
                 85                  90                  95

Asn Gly Tyr Cys
            100
```

<210> SEQ ID NO 10
<211> LENGTH: 199
<212> TYPE: PRT
<213> ORGANISM: Bordetella pertussis

<400> SEQUENCE: 10

```
Ala Val Ala Pro Gly Ile Val Ile Pro Pro Lys Ala Leu Phe Thr Gln
  1               5                  10                  15

Gln Gly Gly Ala Tyr Gly Arg Cys Pro Asn Gly Thr Arg Ala Leu Thr
             20                  25                  30

Val Ala Glu Leu Arg Gly Asn Ala Glu Leu Gln Thr Tyr Leu Arg Gln
         35                  40                  45

Ile Thr Pro Gly Trp Ser Ile Tyr Gly Leu Tyr Asp Gly Thr Tyr Leu
     50                  55                  60

Gly Gln Ala Tyr Gly Gly Ile Ile Lys Asp Ala Pro Pro Gly Ala Gly
 65                  70                  75                  80

Phe Ile Tyr Arg Glu Thr Phe Cys Ile Thr Thr Ile Tyr Lys Thr Gly
```

-continued 85 90 95

Gln Pro Ala Ala Asp His Tyr Tyr Ser Lys Val Thr Ala Thr Arg Leu
100 105 110

Leu Ala Ser Thr Asn Ser Arg Leu Cys Ala Val Phe Val Arg Asp Gly
115 120 125

Gln Ser Val Ile Gly Ala Cys Ala Ser Pro Tyr Glu Gly Arg Tyr Arg
130 135 140

Asp Met Tyr Asp Ala Leu Arg Arg Leu Leu Tyr Met Ile Tyr Met Ser
145 150 155 160

Gly Leu Ala Val Arg Val His Val Ser Lys Glu Glu Gln Tyr Tyr Asp
165 170 175

Tyr Glu Asp Ala Thr Phe Gln Thr Tyr Ala Leu Thr Gly Ile Ser Leu
180 185 190

Cys Asn Pro Ala Ala Ser Ile
195

<210> SEQ ID NO 11
<211> LENGTH: 976
<212> TYPE: PRT
<213> ORGANISM: Bordetella pertussis

<400> SEQUENCE: 11

Met Arg Cys Thr Arg Ala Ile Arg Gln Thr Ala Arg Thr Gly Trp Leu
1 5 10 15

Thr Trp Leu Ala Ile Leu Ala Val Thr Ala Pro Val Thr Ser Pro Ala
20 25 30

Trp Ala Asp Asp Pro Pro Ala Thr Val Tyr Arg Tyr Asp Ser Arg Pro
35 40 45

Pro Glu Asp Val Phe Gln Asn Gly Phe Thr Ala Trp Gly Asn Asn Asp
50 55 60

Asn Val Leu Asp His Leu Thr Gly Arg Ser Cys Gln Val Gly Ser Ser
65 70 75 80

Asn Ser Ala Phe Val Ser Thr Ser Ser Ser Arg Arg Tyr Thr Glu Val
85 90 95

Tyr Leu Glu His Arg Met Gln Glu Ala Val Glu Ala Glu Arg Ala Gly
100 105 110

Arg Gly Thr Gly His Phe Ile Gly Tyr Ile Tyr Glu Val Arg Ala Asp
115 120 125

Asn Asn Phe Tyr Gly Ala Ala Ser Ser Tyr Phe Glu Tyr Val Asp Thr
130 135 140

Tyr Gly Asp Asn Ala Gly Arg Ile Leu Ala Gly Ala Leu Ala Thr Tyr
145 150 155 160

Gln Ser Glu Tyr Leu Ala His Arg Arg Ile Pro Pro Glu Asn Ile Arg
165 170 175

Arg Val Thr Arg Val Tyr His His Gly Ile Thr Gly Glu Thr Thr Thr
180 185 190

Thr Glu Tyr Ser Asn Ala Arg Tyr Val Ser Gln Gln Thr Arg Ala Asn
195 200 205

Pro Asn Pro Tyr Thr Ser Arg Arg Ser Val Ala Ser Ile Val Gly Thr
210 215 220

Leu Val Arg Met Ala Pro Val Ile Ser Ala Cys Met Ala Arg Gln Ala
225 230 235 240

Glu Ser Ser Glu Ala Met Ala Ala Trp Ser Glu Arg Ala Gly Glu Ala
245 250 255

-continued

```
Met Val Leu Val Tyr Tyr Glu Ser Ile Ala Tyr Ser Phe Val Met Pro
            260                 265                 270

Ile Asp Arg Lys Thr Leu Cys His Leu Leu Ser Val Leu Pro Leu Ala
        275                 280                 285

Leu Leu Gly Ser His Val Ala Arg Ala Ser Thr Pro Gly Ile Val Ile
    290                 295                 300

Pro Pro Gln Glu Gln Ile Thr Gln His Gly Ser Pro Tyr Gly Arg Cys
305                 310                 315                 320

Ala Asn Lys Thr Arg Ala Leu Thr Val Ala Glu Leu Arg Gly Ser Gly
                325                 330                 335

Asp Leu Gln Glu Tyr Leu Arg His Val Thr Arg Gly Trp Ser Ile Phe
            340                 345                 350

Ala Leu Tyr Asp Gly Thr Tyr Leu Gly Gly Glu Tyr Gly Gly Val Ile
        355                 360                 365

Lys Asp Gly Thr Pro Gly Gly Ala Phe Asp Leu Lys Thr Thr Phe Cys
    370                 375                 380

Ile Met Thr Thr Ala His Thr Gly Gln Pro Ala Thr Asp His Val Tyr
385                 390                 395                 400

Ser His Val Thr Ala Thr Arg Leu Leu Ser Ser Thr His Ser Arg Leu
                405                 410                 415

Cys Ala Val Phe Val Arg Ser Gly Gln Pro Val Ile Gly Ala Cys Thr
            420                 425                 430

Ser Pro Tyr Asp Gly Lys Tyr Trp Ser His Tyr Ser Arg Leu Arg Lys
        435                 440                 445

Met Leu Tyr Leu Ile Tyr Val Ala Gly Ile Ser Val Arg Val His Val
    450                 455                 460

Ser Lys Glu Glu Gln Tyr Tyr Asp Tyr Glu Asp Ala Thr Phe Glu Thr
465                 470                 475                 480

Tyr Ala Leu Thr Gly Ile Ser Ile Cys His Pro Gly Ser Ser Leu Cys
                485                 490                 495

Val Ala Trp Leu Leu Ala Ser Gly Ala Met Thr His Leu Ser Pro Ala
            500                 505                 510

Leu Ala Asp Val Pro Tyr Val Leu Val Lys Thr His His Val Val Thr
        515                 520                 525

Ser Val Ala His Lys Pro Val Glu Val Thr Pro Thr Arg Met Leu Val
    530                 535                 540

Cys Gly Ile Ala Ala Lys Leu Gly Ala Ala Ala Ser Ser Pro Asp Ala
545                 550                 555                 560

His Val Pro Phe Cys Phe Gly Lys Asp Leu Lys Arg Pro Gly Ser Ser
                565                 570                 575

Pro His Glu Val Met Leu Arg Ala Val Phe Met Gln Gln Arg Pro Leu
            580                 585                 590

Arg Met Phe Leu Gly Pro Lys Gln Leu Thr Phe Glu Gly Lys Pro Ala
        595                 600                 605

Leu Glu Leu Ile Arg Met Val Glu Cys Ser Gly Lys Gln Asp Cys Pro
    610                 615                 620

Val Phe Met His Thr Ile Ala Ser Ile Leu Leu Ser Val Leu Gly Ile
625                 630                 635                 640

Tyr Ser Pro Ala Asp Val Ala Gly Leu Pro Thr His Leu Tyr Lys Asn
                645                 650                 655

Phe Thr Val Gln Glu Leu Ala Leu Lys Leu Lys Gly Lys Asn Gln Glu
            660                 665                 670

Phe Cys Leu Thr Ala Phe His Ser Gly Arg Ser Leu Val Arg Ala Cys
```

-continued

```
        675                 680                 685

Leu Ser Asp Ala Gly His Glu His Asp Thr Trp Phe Asp Thr Met Leu
    690                 695                 700

Gly Phe Ala Ile Ser Ala Tyr Ala Leu Lys Ser Arg Ile Ala Leu Thr
705                 710                 715                 720

Val Glu Asp Ser Pro Tyr Pro Gly Thr Pro Gly Asp Leu Leu Glu Leu
                725                 730                 735

Gln Ile Cys Pro Leu Asn Gly Tyr Cys Glu Val Phe Met Leu Ile Asn
            740                 745                 750

Asn Lys Lys Leu Leu His His Ile Leu Pro Ile Leu Val Leu Ala Leu
        755                 760                 765

Leu Gly Met Arg Thr Ala Gln Ala Val Ala Pro Gly Ile Val Ile Pro
    770                 775                 780

Pro Lys Ala Leu Phe Thr Gln Gln Gly Gly Ala Tyr Gly Arg Cys Pro
785                 790                 795                 800

Asn Gly Thr Arg Ala Leu Thr Val Ala Glu Leu Arg Gly Asn Ala Glu
                805                 810                 815

Leu Gln Thr Tyr Leu Arg Gln Ile Thr Pro Gly Trp Ser Ile Tyr Gly
            820                 825                 830

Leu Tyr Asp Gly Thr Tyr Leu Gly Gln Ala Tyr Gly Gly Ile Ile Lys
        835                 840                 845

Asp Ala Pro Pro Gly Ala Gly Phe Ile Tyr Arg Glu Thr Phe Cys Ile
    850                 855                 860

Thr Thr Ile Tyr Lys Thr Gly Gln Pro Ala Ala Asp His Tyr Tyr Ser
865                 870                 875                 880

Lys Val Thr Ala Thr Arg Leu Leu Ala Ser Thr Asn Ser Arg Leu Cys
                885                 890                 895

Ala Val Phe Val Arg Asp Gly Gln Ser Val Ile Gly Ala Cys Ala Ser
            900                 905                 910

Pro Tyr Glu Gly Arg Tyr Arg Asp His Tyr Asp Ala Leu Arg Arg Leu
        915                 920                 925

Leu Tyr Met Ile Tyr Met Ser Gly Leu Ala Val Arg Val His Val Ser
    930                 935                 940

Lys Glu Glu Gln Tyr Tyr Asp Tyr Glu Asp Ala Thr Phe Gln Thr Tyr
945                 950                 955                 960

Ala Leu Thr Gly Ile Ser Leu Cys Asn Pro Ala Ala Ser Ile Cys Val
                965                 970                 975


<210> SEQ ID NO 12
<211> LENGTH: 8
<212> TYPE: PRT
<213> ORGANISM: Bordetella pertussis

<400> SEQUENCE: 12

Tyr Arg Tyr Asp Ser Arg Pro Pro
  1               5


<210> SEQ ID NO 13
<211> LENGTH: 8
<212> TYPE: PRT
<213> ORGANISM: Vibrio cholerae

<400> SEQUENCE: 13

Tyr Arg Ala Asp Ser Arg Pro Pro
  1               5
```

-continued

<210> SEQ ID NO 14
<211> LENGTH: 8
<212> TYPE: PRT
<213> ORGANISM: Escherichia coli

<400> SEQUENCE: 14

Tyr Arg Ala Asp Ser Arg Pro Pro
1 5

<210> SEQ ID NO 15
<211> LENGTH: 8
<212> TYPE: PRT
<213> ORGANISM: Bordetella pertussis

<400> SEQUENCE: 15

Val Ser Thr Ser Ser Ser Arg Arg
1 5

<210> SEQ ID NO 16
<211> LENGTH: 8
<212> TYPE: PRT
<213> ORGANISM: Vibrio cholerae

<400> SEQUENCE: 16

Val Ser Thr Ser Ile Ser Leu Arg
1 5

<210> SEQ ID NO 17
<211> LENGTH: 8
<212> TYPE: PRT
<213> ORGANISM: Escherichia coli

<400> SEQUENCE: 17

Val Ser Thr Ser Leu Ser Leu Arg
1 5

<210> SEQ ID NO 18
<211> LENGTH: 7
<212> TYPE: DNA
<213> ORGANISM: Escherichia coli

<400> SEQUENCE: 18 taaaata 7

<210> SEQ ID NO 19
<211> LENGTH: 7
<212> TYPE: DNA
<213> ORGANISM: Escherichia coli

<400> SEQUENCE: 19 tataata 7

<210> SEQ ID NO 20
<211> LENGTH: 6
<212> TYPE: DNA
<213> ORGANISM: Escherichia coli

<400> SEQUENCE: 20 ctgacc 6

<210> SEQ ID NO 21
<211> LENGTH: 6
<212> TYPE: DNA
<213> ORGANISM: Escherichia coli -continued

<400> SEQUENCE: 21 ttgaca 6

<210> SEQ ID NO 22
<211> LENGTH: 7
<212> TYPE: DNA
<213> ORGANISM: Escherichia coli

<400> SEQUENCE: 22 ggggaag 7

<210> SEQ ID NO 23
<211> LENGTH: 7
<212> TYPE: DNA
<213> ORGANISM: Escherichia coli

<400> SEQUENCE: 23 aaggagg 7

<210> SEQ ID NO 24
<211> LENGTH: 9
<212> TYPE: DNA
<213> ORGANISM: Escherichia coli

<400> SEQUENCE: 24 cagggcggc 9

<210> SEQ ID NO 25
<211> LENGTH: 6
<212> TYPE: DNA
<213> ORGANISM: Escherichia coli

<400> SEQUENCE: 25 aaggcg 6

<210> SEQ ID NO 26
<211> LENGTH: 6
<212> TYPE: DNA
<213> ORGANISM: Escherichia coli

<400> SEQUENCE: 26 aaggag 6

<210> SEQ ID NO 27
<211> LENGTH: 8
<212> TYPE: DNA
<213> ORGANISM: Escherichia coli

<400> SEQUENCE: 27 gggaacac 8

<210> SEQ ID NO 28
<211> LENGTH: 8
<212> TYPE: DNA
<213> ORGANISM: Escherichia coli

<400> SEQUENCE: 28 gggaagac 8

PERTUSSIS TOXIN GENE: CLONING AND EXPRESSION OF PROTECTIVE ANTIGEN

This application is a continuation of application Ser. No. 09/792,861 filed on Feb. 23, 2001, now abandoned, which is a continuation of application Ser. No. 08/483,326 filed on Jun. 7, 1995, now abandoned, which is a continuation of application Ser. No. 07/542,149 filed on Jun. 22, 1990, which is a continuation of application Ser. No. 07/311,612 filed on Feb. 15, 1989, now abandoned.

The present invention is related to molecular cloning of pertussis toxin genes capable of expressing an antigen peptide having substantially reduced enzymatic activity while being protective against pertussis. More particularly, the present invention is related to bacterial plasmids pPTX42 and pPTXS1/6A encoding pertussis toxin.

STATE OF THE ART

Pertussis toxin is one of the various toxic components produced by virulent *Bordetella pertussis*, the microorganism that causes whooping cough. A wide variety of biological activities such as histamine sensitization, insulin secretion, lymphocytosis promoting and immuno-potentiating effects can be attributed to this toxin. In addition to these activities, the toxin provides protection to mice when challenged intracerebrally or by aerosol. Pertussin toxin is, therefore, an important constituent in the vaccine against whooping cough and is included as a component in such vaccines.

However, while this is one of the major protective antigens against whooping cough, it is also associated with a variety of pathophysiological activities and is believed to be the major cause of harmful side effects associated with the present pertussis vaccine. In most recipients these side effects are limited to local reactions, but in rare cases neurological damage and death does occur (Baraff et al, 1979 in Third International Symposium on Pertussis. U.S. HEW publication No. NIH-79-1830). Thus a need to produce a new generation of vaccine against whooping cough is evident.

SUMMARY OF THE INVENTION

It is, therefore, an object of the present invention to clone the gene(s) responsible for expression of pertussis toxin.

It is a further object of the present invention to isolate at least a part of the pertussis toxin genome and determine the nucleotide sequence and genetic organization thereof.

It is yet another object of the present invention to characterize the toxin polypeptide encoded by the cloned gene(s), at least in terms of the amino acid sequence thereof.

Others objects and advantages of the present invention will become evident upon a reading of the detailed description of the invention presented herein.

BRIEF DESCRIPTION OF DRAWINGS

These and other objects, features and many of the attendant advantages of the invention will be better understood upon a reading of the following detailed description when considered in connection with the accompanying drawings wherein.

FIG. 1 shows SDS-electrophoresis of the products of HPLC separation of pertussis toxin. Lanes 1 and 12 contain 5 μg and 10 μg, respectively, of unfractionated pertussis toxin. Lanes 2 through 11 contain 100 μl aliquots of elution fractions 19 through 28, respectively. The molecular weights of the subunits are indicated:

FIG. 3 shows Southern blot analysis of *B. pertussis* genomic DNA with cloned DNA probes. (a) Total genomic DNA from strain 3779 was digested with various restriction enzymes as indicated on the figure, and analyzed by Southern blot using nick translated PstI fragment B of pPTX42 (see FIG. 2*c*). (b) Between 24 μg and 60 μg of genomic DNA from strains 3779, Sakairi (pertussis toxin$^-$, Tn5$^-$), BP347 (non-virulent, Tn5$^+$), BP349 (hemolysin$^-$, Tn5$^+$), BP353 (filamentous hemagglutinin$^-$, Tn5$^+$), BP356 and BP357 (both pertussis toxin$^-$, Tn$^+$) (15) (lanes 1 through 7, respectively) were digested with PstI and analyzed by Southern blot using nick translated PstI fragment B as the probe. (c) The same as panel b except PstI fragment C was used as the probe;

DETAILED DESCRIPTION OF INVENTION

Figures 2A, 2B, 2C:
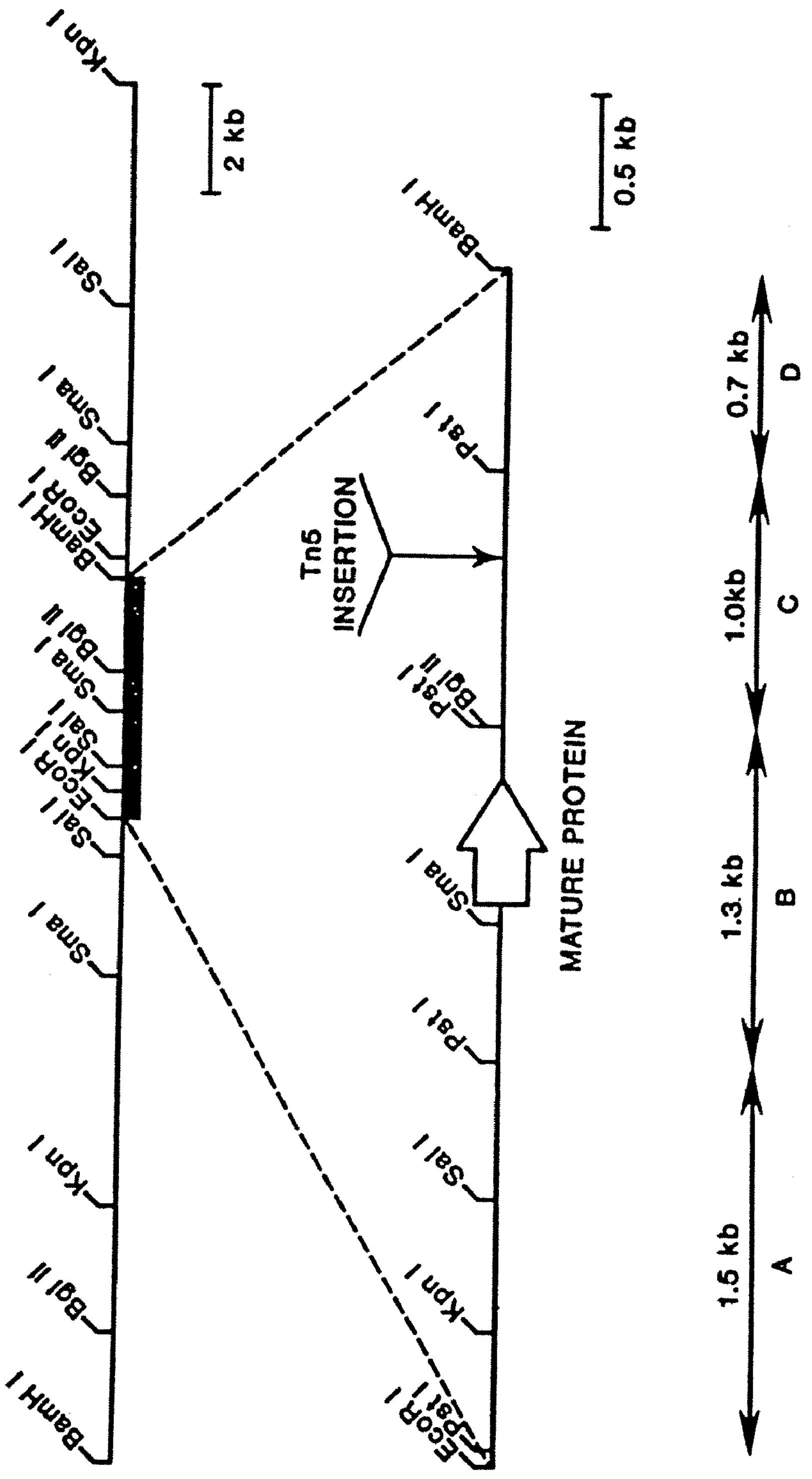
FIG. 2 shows restriction map of the cloned 4.5 kb EcoRI/BamHI *B. pertussis* DNA fragment and genomic DNA in the region of the pertussis toxin subunit gene. (a) Restriction map of a 26 kb region of *B. pertussis* genomic DNA containing pertussis toxin genes. (b) Restriction map of the 4.5 kb EcoRI/BamHI insert from pPTX42. The arrow indicates the start and translation direction of the mature toxin subunit. The location of the Tn5 DNA insertion in mutant strains BP356 and BP357 is shown. (c) PstI fragment derived from the insert shown in panel b.

The above objects and advantages of the present invention are achieved by molecular cloning of pertussis toxin genes. The cloning of the gene provides means for genetic manipulation thereof and for producing new generation of substantially pure and isolated form of antigenic peptides (toxins) for the synthesis of new generation of vaccine against pertussis. Of course, such manipulation of the pertussis toxin gene and the creation of new, manipulated toxins retaining antigenicity against pertussis but being devoid of undesirable side effects was not heretofore possible. The present invention is the first to clone the pertussis toxin gene in an expression vector, to map its nucleotide sequence and to disclose the finger print of the polypeptide encoded by said gene(s).

Any vector wherein the gene can be cloned by recombination of genetic material and which will express the cloned gene can be used, such as bacterial (e.g., gt11), yeast (e.g. pGPD-1), viral (e.g. pGS 20 or pMM4) and the like. A preferred vector is the microorganism *E. coli* wherein the pertussis gene has been cloned in the plasmid thereof.

Although any similar or equivalent methods and materials could be used in the practice or testing of the present invention, the preferred methods and materials are now described. All scientific and/or technical terms used herein have the same meaning as generally understood by one of ordinary skill in the art to which the invention belongs. All references cited hereunder are incorporated herein by reference.

Materials and Methods

Materials. Restriction enzymes were purchased from Bethesda Research Laboratories (BRL) or International Biotechnologies, Inc. and used under conditions recommended by the suppliers. T4 DNA ligase, M13mp19 RF vector, isopropylthio-β-galactoside (IPTG), 5-bromo-4-chloro-3-indolyl-β-D-galactoside (X-Gal), the 17-bp universal primer, Klenow fragment (Lyphozyme$^R$) and T4 polynucleotide kinase were purchased from BRL. Calf intestine phosphatase was obtained from Boehringer Mannheim, nucleotides from PL-Biochemicals and base modifying chemicals from Kodak (dimethylsulfate, hydrazine and piperidine) and EM Science (formic acid). Plasmid pMC1403 and *E. coli* strain JM101 (supE, thi, Δ(lac-proAB), [F', traD36, proAB, lacI Z ΔM15]) were obtained from Dr. Francis Nano (Rocky Mountain Laboratories, Hamilton, Mont.). Elutip-d$^R$ columns came from Schleicher & Schuell and low melting point agarose from BRL. Radiochemicals were supplied by ICN Radiochemicals (crude γ-$^{32}$P]ATP, 7000 Ci/mmol) and NEN Research Products ([∝-$^{32}$P]dGTP, 800 Ci/mmole). *B. pertussis* strain 3779 was obtained from Dr. John J. Munoz, Rocky Mountain Lab, Hamilton, Mont. This strain is also known as 3779 BL2S4 and is commonly available.

Purification of Pertussin Toxin Subunits

Pertussis toxin from *B. Pertussis* strain 3779 was prepared by the method of Munoz et al, Cell Immunol. §3:92-100, 1984. Five mg of the toxin was resuspended in trifluoroacetic acid and fractionated by high pressure liquid chromatography, HPLC, using a 1×25 cm Vydac C-4 preparative column. The sample was injected in 50% trifluoroacetic acid and eluted at 4 ml/min over 30 min with a linear gradient of 25% to 100% acetonitrile solution containing 66% acetonitrile and 33% isopropyl alcohol. All solutions contained 0.1% trifluoroacetic acid. Elution was monitored at 220 nm and two ml fractions collected. Aliquots of selected fractions were dried by evaporation, resuspended in gel loading buffer containing 2-mercaptoethanol and analyzed by sodium dodecylsulphate polyacrylamide gel electrophoresis, SDS-PAGE, on a 12% gel.

Protein and DNA Sequencing: The polypeptide from HPLC fraction 21 (FIG. 1, lane 4) was sequenced using a Beckman 890C automated protein sequenator according to the methods described by Howard et al, Mol. Biochem. Parasit. 12:237-246, 1984. DNA was sequenced from the SmaI site (see FIG. 2*b*) by the Maxam and Gilbert technique as described in Methods in Enzymol. 65:499-560, 1980.

Isolation of Pertussis Toxin Genes: Chromosomal DNA was prepared from *B. pertussis* strain 3779 following the procedure described by Hull et al, Infec. Immunol. 33:933, 1981. The DNA was digested with both endonucleases EcoRI and BamHI and ligated into the same sites in the polylinker of pMC1403 as described by Casadaban et al. J. Bacteriol. 143:971-980, 1983; Maniatis et al, Molecular Cloning: A Laboratory Manual, 1982. The conditions for ligation were: 60 ng of vector DNA and 40 ng of inset DNA incubated with 1.5 units of T4 DNA ligase (BRL) and 1 mM ATP and 15° C. for 20 h. *E. coli* JM109 cells were transformed with the recombinant plasmid in accordance with the procedure of Hanahan, J. Mol. Biol. 166:557-580, 1983 and clones containing the toxin gene identified by colony hybridization at 37° C. using a $^{32}$P-labeled 17-base mixed oligonucleotide probe 21D3 following the procedure of Woods, Focus 6:1-3, 1984. The probe was synthesized on a SAM-1 DNA synthesizer (Biosearch, San Rafael, Calif.) and consisted of the 32 possible oligonucleotides coding for 6 consecutive amino acids of the pertussis toxin subunit (Table 1). The probe was purified from a 20% urea-acrylamide gel and 5'-end labeled using 0.2 mCi of (gamma$^{32}$P)ATP (ICN, crude, 7000 Ci/mmol) and 1 unit of $T_4$ polynucleotide kinase (BRL) per 10 μl of reaction mixture in 50 mM Tris-HCl (pH 7.4) 5 mM DTT, 10 mM $MgCl_2$. The labeled oligonucleotides were purified by binding to a DEAE-cellulose column (DE52, Whatman) in 10 mM Tris-HCl (pH 7.4), 1 mM EDTA (TE) and eluted with 1.0 M NaCl in TE. Ten positive clones were isolated and purified. Plasmid DNA from these clones were extracted according to the procedure of Maniatis et al, Molecular Cloning: A Laboratory Manual, 1982, digested with routine restriction endonucleases (BRL), and then analyzed by 0.8% agarose gel electrophoresis in TBE (10 mM Trisborate pH 8.0, 1 mM EDTA). Southern blot analysis using the $^{32}$P-labeled oligonucleotide 21D3 as the probe showed that all 10 clones contained an identical insert of *B. pertussis* DNA. One clone was used for further analysis by Southern blots (FIG. 3) and for DNA sequencing.

Southern Blot Analyses: Extracted DNA as described supra, was digested and separated by electrophoresis using either 0.7% or 1.2% agarose gels in 40 mM Tris-acetate pH 8.3, 1 mM Tris-acetate pH 8.3, 1 mM EDTA for 17 h at 30 V. The DNA was then blotted onto nitrocellulose in 20×SSPE, sodium chloride, sodium phosphate EDTA buffer, pH 7.4, in accordance with Maniatis et al., supra, and baked at 80° C. in a vacuum oven for 2 h. Filters were prehybridized at 68° C. for 4 h in 6×SSPE, 0.5% SDS, 5× modified Denhardt's (0.1% Ficoll 400, 0.1% bovine serum albumin, 0.1% polyvinylpyrrolidone and 0.3×SSPE) and 100 μg/ml denatured herring sperm DNA. The hybridization buffer was the same as the prehybridization buffer, except EDTA was added to a final concentration of 10 mM. PstI fragments A, B, C and D were isolated by 0.8% low-melting point agarose gel electrophoresis, purified on Elutip-d columns (Schleicher and Schuell) and nick translated (BRL) using (alpha$^{32}$P)CTP (800 Ci/mmol, NEN Research Products). The nick translated probes were hybridized at a concentration of about 1 μCi/ml for 48 h at 68° C. Filters were then washed in 2×SSPE and 0.5% SDS at room (22°-25° C.) temperature for 5 min, then in 2×SSPE and 0.1% SDS at room temperature for 5 min, then in 2×SSPE and 0.1% SDS at room temperature for 15 min, and finally in 0.1×SSPE and 0.5% SDS at 68° C. for 2 h. The washed filters were air dried and exposed to X-ray film using a Lightning-Plus intensifying screen following standard techniques.

Isolation and cloning of S4 subunit gene: As mentioned above, purified pertussis toxin from *B. pertussis* strain 3779 was fractionated by high pressure liquid chromatography (HPLC). One fraction (F-21) contained a polypeptide which comigrated as a major band with subunit S4 on SDS-PAGE (FIG. 1, lane 4). Although complete separation was not achieved, the major portion of the other toxin subunits were recovered in other HPLC fractions, i.e., S2 in Fr22, S1 and S5 in Fr23, and S3 in Fr24 (FIG. 1). The amino acid sequence of the first 30 $NH_2$-terminal residues of the protein in fraction 21 was determined and is shown in Table 1.

examined by restriction enzyme and Southern blot analyses. All 10 colonies contained a recombinant plasmid with an identical 4.5 kb EcoRI/BamHI pertussis DNA insert. One of these clones, identified as pPTX42, was selected for further characterization. A restriction map of the insert DNA was prepared and is shown in FIG. 2*b*; Southern blot analysis indicated that the oligonucleotide probe 21D3 hybridized to only the 0.8 kb SmaI/PstI fragment.

A deposit of said pPTX42 clone has been made in American Type Culture Collection, Rockville, Md. under the accession No. 67046. This culture will continue to be maintained for at least 30 years after a patent issues and will

TABLE 1

Protein and DNA Sequences of Pertussis Toxin Subunit, Oligonucleotide Probe and Homologous Genomic DNA Clone

| | |
|---|---|
| | Sma I f-Met |
| DNA sequence: | C CCG GGA CAG GGC GGC GCC CGG CGG TCG CGG GTG CGC GCC CTG- |
| Predicted amino sequence: | Pro Gly Gln Gly Gly Ala Arg Arg Ser Arg Val Arg Ala Leu- |
| | -30 -20 |
| | f-Met f-Met |
| | GCG TGG TTC CTG GCA TCC GGC GCG ATG ACG CAT CTT TCC CCC GCC CTG- |
| | Ala Trp Leu Leu Ala Ser Gly Ala Met Thr His Leu Ser Pr Ala Leu- |
| | -10 |
| | GCC GAC GTT CCT TAT GTG CTG GTG AAG ACC AAT ATG GTG GTC ACC AGC- |
| | Ala*Asp Val Pro Tyr Val Leu Val Lys Thr Asn Met Val Val Thr Ser- |
| Mature protein sequence: | $H_2N$ -Asp Val Pro Tyr Val Leu Val Lys Thr Asn Met Val Val Thr (?)- |
| | 1 10 |
| | probe 21D3 |
| | ATG AAP CCN TAY GAP GT |
| | GTA GCC ATG AAG CCG TAT GAA GTC ACC CCG ACG CGC ATG CTG GTC- |
| | Val Ala Met Lys Pro Tyr Glu Val Thr Pro Thr Arg Met Leu Val- |
| | Val Ala Met Lys Pro Tyr Glu Val(Val)Pro(Pro)Arg Met Leu Val- |
| | 20 30 |

The S4 $H_2N$-terminal amino acid sequence determined using the automated protein sequenator is shown in blocks as the mature protein sequence. Residues that were questionable in the sequence are indicated by brackets. The DNA and predicted amino acid sequences are shown. P ssible initiation c dons are indicated by f-Met. A putative proteolytic cleavage site is indicated by *. The lig nucleotide probe sequence is shown in the bl ck labeled probe 21D3.The abbreviati ns used are: P = G or A; Y = T r C; N = A, C, G or T.

Based on the protein sequence shown in Table 1, a mixed oligonucleotide probe representing a region of six consecutive amino acids with the least redundancy of the genetic code was synthesized. In this mixture of oligonucleotides, identified as probe 21D3, approximately 1 out of 32 molecules corresponds to the actual DNA sequence of the pertussis toxin gene (Table 1). This mixed oligonucleotide probe was used to screen a DNA clone bank containing restriction fragments of total pertussis chromosomal DNA. The clone bank was prepared by digesting genomic DNA isolated from *B. pertussis* strain 3779 with both EcoRI and BamHI restriction endonucleases. The complete population of restriction fragments was ligated into the EcoRI/BamHI restriction site of expression vector pMC1403 and the recombinant plasmid used to transform *E. coli* JM109 cells following standard procedures well known in the art. It is noted that although *E. coli* is the preferred organism, other cloning vectors well known in the art, could, of course, be alternatively used.

Approximately 20,000 colonies were screened by colony hybridization using the 32P-end labeled oligonucleotide probe 21D3. The plasmid DNA of 10 positive colonies was be available to the public without restriction, of course, in accordance with the provisions of the law.

Sequencing of the $N_2$H-terminal region for S4: The 0.8 kb fragment was isolated by agarose gel electrophoresis and sequenced using the Maxam and Gilbert technique, supra. The DNA sequence was translated into an amino acid sequence and a portion of that sequence is compared in Table 1 to the $NH_2$-terminal 30 amino acids of the pertussis toxin subunit and the oligonucleotide probe 21D3 sequence. Out of the sequence of 30 amino acid residues determined using the automated sequenator, only 2 do not correspond to the amino acid sequence deduced from the DNA sequence, i.e., residues 24 and 26 are questionable because they repeat the amino acid in front of them and they are located near the end of the analyzed sequence. Amino acid 15 could not be determined. The rest of the deduced amino acid sequence perfectly matches the original protein sequence. The oligonucleotide probe sequence also perfectly matches the cloned DNA sequence. These results indicate that at least one of the pertussis toxin subunit genes has been cloned.

Examination of the DNA sequence indicates that a precursor protein, perhaps containing a leader sequence, may exist (Table 1). In fact, the $NH_2$-terminal aspartic acid of the mature protein is not immediately preceded by one of the known initiation codons, i.e., ATG, GTG, TTG, or ATT, but by GCC coding for alanine, an amino acid that often occurs at the cleavage site of a signal peptide. A proline is found at amino acid position −4, which is also consistent with cleavage sites in other known sequences where this amino acid is usually present within six residues of the cleavage site. Possible translation initiation sites in the same reading frame as the mature protein and upstream of the $NH_2$-terminal aspartic acid are: ATG at position −9, TTG at −15 and GTG at −21; however, none of these are preceded by a Shine/Dalgarno ribosomal binding site (Nature, London, 254:34-38, 1975) and only CTG at −21 is immediately followed by a basic amino acid (arginine) bacterial signal sequences. Using the DNA sequence data and primer extension to sequence the mRNA, the actual initiation site could also be determined.

Physical mapping of the S4 gene on the bacterial chromosome: The 1.3 kb PstI fragment B containing at least part of the pertussis toxin gene was used as a probe to physically map the location of this gene on the *B. pertussis* genome (FIG. 2). FIG. 3*a* shows a Southern blot analysis of total *B. pertussis* DNA digested with a variety of six base pair-specific restriction enzymes and probed with the 1.3 kb PstI fragment B isolated from pPTX42. Each restriction digest yielded only one DNA band which hybridized with the probe. Since the 1.3 kb PstI fragment B contains a SmaI site, two bands would be expected from a SmaI digest of genomic DNA unless the SmaI fragments were similar in size. Further analysis indicated that the single band seen in the SmaI digest is actually a doublet of two similar size DNA fragments. In this particular gel, fragments of 1.3 kb and smaller migrated off the gel during electrophoresis and thus could not be detected; however, in other Southern blots in which no fragment was run off the gel, only one band was found for each restriction enzyme. These results indicate that the gene encoded by the PstI fragment B occurs only once in the genome. Using the data from these experiments and similar studies using the 1.5 kb PstI fragment A and the 0.7 kb PstI/BamHI fragment D from the cloned 4.5 kb EcoRI/BamHI fragment D from the cloned 4.5 kb EcoRI/BamHI fragment, a partial restriction map of a 26 kb region of the pertussis genome as shown in FIG. 2*a* was obtained. This method allowed to locate the first restriction site of a particular endonuclease on either side of the 4.5 kb EcorRi/BamHI fragment. This information is useful in deciphering the genetic arrangement of the toxin gene and for the cloning of larger DNA fragments of pertussis toxin.

Relationship of the S4 gene and Tn5-insertions: Weiss et al., Infect. Immun. 42:33-41, 1983, have developed several important Tn5-induced *B. pertussis* mutants deficient in different virulence factors, i.e., pertussis toxin, hemolysin, and filamentous hemagglutinin (Infect. Immun. 43:263-269, 1984; J. Bacteriol. 153:304-309, 1983). To investigate the physical relationship between the Tn5 DNA insertion and the pertussis toxin subunit gene, genomic DNA from these mutants and strain 3779 by Southern blots using various restriction fragments of the cloned 4.5 kb EcoRI/BamHI DNA fragment as probes were analyzed. In one set of experiments, blots of genomic PstI fragments were separately probed with cloned PstI fragments A, B, C, and D (FIG. 2*c*). The PstI fragments from the mutants and strain 3779 which hybridized with the cloned PstI fragments A, B, and D were exactly the same size; the blot probed with PstI fragment B is shown in FIG. 3*b*. However, when the PstI fragment C was used as a probe, the genomic DNA from mutant strains BP356 and BP357 showed a clear difference in the size of the PstI fragments that hybridized as compared to strain 3779 and the other mutant strains (FIG. 3*c*, lanes 6 and 7). These results indicate that this fragment contains the site of the Tn5 insertion. As expected, two labeled fragments were found, since the Tn5 DNA insert has two symmetrical PstI sites. Other Southern blots (not shown) in which genomic BglII and SmaI fragments were hybridized with the 4.5 kb EcoRI/BamHI cloned probe, and the data from FIG. 3*c*, clearly show that the Tn5 DNA was inserted 1.3 kb downstream from the start of the mature pertussis toxin S4 subunit in the two mutant strains that were characterized as pertussis toxin negative phenotypes, i.e., BP356 and BP357 (FIG. 2*b*). This insertion is beyond the termination codon for the S4 subunit (11.7 kD). Examination of these toxin negative mutants by Western blots using monoclonal antibodies for individual subunits indicate that the Tn5 DNA is not inserted in the subunit structural genes for S1 and S2 (unpublished results). The pertussis toxin negative phenotype of strains BP356 and BP357 can be explained by either of two nonexclusive mechanisms. The Tn5 DNA may be inserted into the coding regions of either S3, S5, or perhaps another gene required for toxin assembly or transport. Alternatively, the Tn5 insertion could disrupt the expression of essential downstream cistrons in a polycistronic operon. Similar Southern blot analyses of genomic BamHI and EcoRI fragments indicate that none of the other virulence factor genes represented by the other Tn5-insertion mutants, are located within the 17 Kb region defined by the first BamHI and the second EcoRI sites as shown in FIG. 2*a*.

Nucleotide Sequence

Figure 4A:
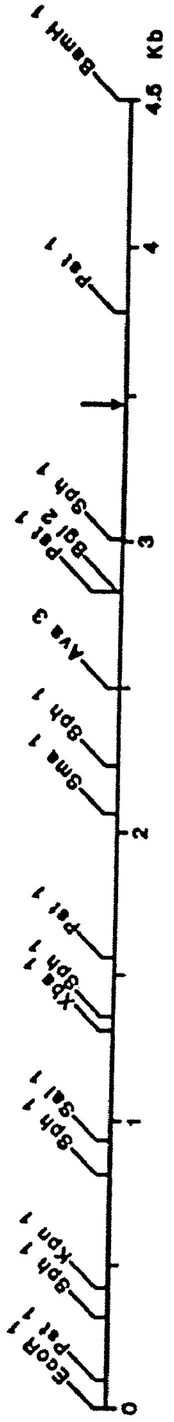
FIG. 4 shows the physical map and genetic organization of the Pertussis Toxin Gene. (a) Restriction map of the 4.5 kb EcoRI/BamHI fragment from pPTX42 containing the pertussis toxin gene cloned from *B. pertussis* strain 3779 (12). The arrow indicates the position of the Tn5 DNA insertion in pertussis toxin negative Tn5-induced mutant strains BP356 and BP357 (24). (b) Open reading frames in the forward direction. c) Open reading frames in the backward direction. The vertical lines indicates termination codons. d) Organization map of the pertussis toxin gene. The arrows show the translational direction and length of the protein coding regions for the individual subunits. The hatched boxes represent the signal peptides. The solid bars in S1 represent the regions homologous to the A subunits in cholera and *E. coli* heat labile toxins.
Figure 4B:
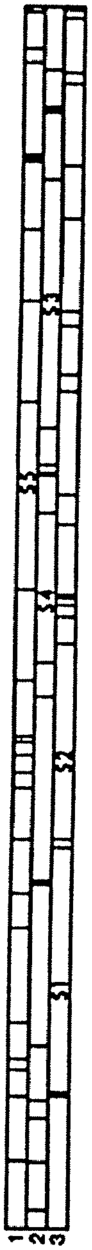
Figure 4C:
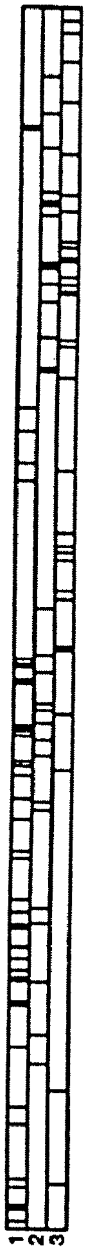

Having described the identification, isolation, and construction of recombinant plasmid pPTX42, containing pertussis toxin genes, the insert DNA from this plasmid, i.e., the 4.5 kb EcoRI/BamHI fragment shown in FIG. 4*a*, was digested with various restriction enzymes and subcloned by standard procedures (Maniatis et al., supra) using the cloning vectors M13 mp18 and M13 mp19 and *E. coli* strain JM101 as described by Messing, Methods Enzymol. 101: 20-78, 1983. Both strands of the DNA were sequenced using either the Maxam and Gilbert base-specific chemical cleavage method, supra, or the dideoxy chain termination method of Sanger et al., PNAS, 74:5463-5467, 1977, with the universal 17-base primer, or both. The DNA sequence and the derived amino acid sequence were analyzed using MicroGenie™ computer software.

Because of the high C+G content of *B. pertussis* DNA, it was necessary to use both of the above mentioned methods with a combination of 8% and 20% polyacrylamide-8 M urea gels for sequence analysis. Each nucleotide has been sequenced in both directions on average of 4.13 times. The final consensus sequence of the sense strand is shown in Table 2. It is noted that the sequence of the S4 subunit gene has been included in this table for completeness since this sequence lies in the middle of the structural gene sequence presented in Table 2. The entire sequence contains about 62.2% C+G with about 19.6% A, 33.8% C, 28.4% G and 18.2% T in the sense strand, wherein A, T, C and G represent the nucleotides adenine, thymine, cytosine and guanine, respectively.

TABLE 2

Complete Nucleotide Sequence of Pertussis Toxin Gene

```
          .         .         .         .         .         .
CACCCCGACGCGCATGCTGGTCTGCGGCATCGCCGCCAAACTGGGCGCCGCGGCCAGCAG
  T  P  T  R  M  L  V  C  G  I  A  A  K  L  G  A  A  A  S  S
          .      2300         .         .         .         .
CCCGGACGCGCACGTGCCGTTCTGCTTCGGCAAGGATCTCAAGCGTCCCGGCAGCAGTCC
  P  D  A  H  V  P  F  C  F  G  K  D  L  K  R  P  G  S  S  P
          .         .         .         .         .      2400
CATGGAAGTCATGTTGCGCGCCGTCTTCATGCAACAACGGCCGCTGCGCATGTTTCTGGG
  M  E  V  M  L  R  A  V  F  M  Q  Q  R  P  L  R  M  F  L  G
          .         .         .         .         .         .
TCCCAAGCAACTCACTTTCGAAGGCAAGCCCGCGCTCGAACTGATCCGGATGGTCGAATG
  P  K  Q  L  T  F  E  G  K  P  A  L  E  L  I  R  M  V  E  C
          .         .         .   S5-->         .         .
CAGCGGCAAGCAGGATTGCCCCTGAAGGCGAACCCCATGCATACCATCGCATCCATCCTG
  S  G  K  Q  D  C  P  U              fM  H  T  I  A  S  I  L
          .         .         .         .         .         .
TTGTCCGTGCTCGGCATATACAGCCCGGCTGACGTCGCCGGCTTGCCGACCCATCTGTAC
 L  S  V  L  G  I  Y  S  P  A  D  V *A  G  L  P  T  H  L  Y

          .      2600         .         .         .         .
AAGAACTTCACTGTCCAGGAGCTGGCCTTGAAACTGAAGGGCAAGAATCAGGAGTTCTGC
 K  N  F  T  V  Q  E  L  A  L  K  L  K  G  K  N  Q  E  F  C
          .         .         .         .         .      2700
CTGACCGCCTTCATGTCGGGCAGAAGCCTGGTCCGGGCGTGCCTGTCCGACGCGGGACAC
 L  T  A  F  M  S  G  R  S  L  V  R  A  C  L  S  D  A  G  H
          .         .         .         .         .         .
GAGCACGACACGTGGTTCGACACCATGCTTGGCTTTGCCATATCCGCGTATGCGCTCAAG
 E  H  D  T  W  F  D  T  M  L  G  F  A  I  S  A  Y  A  L  K
          .         .         .      2800         .         .
AGCCGGATCGCGCTGACGGTGGAAGACTCGCCGTATCCGGGCACTCCCGGCGATCTGCTC
 S  R  I  A  L  T  V  E  D  S  P  Y  P  G  T  P  G  D  L  L
          .         .         .         .         .         .
GAACTGCAGATCTGCCCGCTCAACGGATATTGCGAATGAACCCTTCCGGAGGTTTCGACG
 E  L  Q  I  C  P  L  N  G  Y  C  E  U
          .      2900         .         .         .         .
TTTCCGCGCAATCCGCTTGAGACGATCTTCCGCCCTGGTTCCATTCCGGGAACACCGCAA
S3-->     .         .         .         .         .      3000
CATGCTGATCAACAACAAGAAGCTGCTTCATCACATTCTGCCCATCCTGGTGCTCGCCCT
fM  L  I  N  N  K  K  L  L  H  H  I  L  P  I  L  V  L  A  L

          .         .         .         .         .         .
GCTGGGCATGCGCACGGCCCAGGCCGTTGCGCCAGGCATCGTCATCCCGCCGAAGGCACT
  L  G  M  R  T  A  Q  A *V  A  P  G  I  V  I  P  P  K  A  L
          .         .         .      3100         .         .
GTTCACCCAACAGGGCGGCGCCTATGGACGCTGCCCGAACGGAACCCGCGCCTTGACCGT
  F  T  Q  Q  G  G  A  Y  G  R  C  P  N  G  T  R  A  L  T  V
          .         .         .         .         .         .
GGCCGAACTGCGCGGCAACGCCGAATTGCAGACGTATTTGCGCCAGATAACGCCCGGCTG
  A  E  L  R  G  N  A  E  L  Q  T  Y  L  R  Q  I  T  P  G  W
          .      3200         .         .         .         .
GTCCATATACGGTCTCTATGACGGTACGTACCTGGGCCAGGCGTACGGCGGCATCATCAA
  S  I  Y  G  L  Y  D  G  T  Y  L  G  Q  A  Y  G  G  I  I  K
          .         .         .         .         .      3300
GGACGCGCCGCCAGGCGCGGGGTTCATTTATCGCGAAACTTTCTGCATCACGACCATATA
  D  A  P  P  G  A  G  F  I  Y  R  E  T  F  C  I  T  T  I  Y
```

TABLE 2-continued

Complete Nucleotide Sequence of Pertussis Toxin Gene

```
         .         .         .         .         .         .
CAAGACCGGGCAACCGGCTGCGGATCACTACTACAGCAAGGTCACGGCCACGCGCCTGCT
  K  T  G  Q  P  A  A  D  H  Y  Y  S  K  V  T  A  T  R  L  L
         .         .         .      3400         .         .
CGCCAGCACCAACAGCAGGCTGTGCGCGGTATTCGTCAGGGACGGGCAATCGGTCATCGG
  A  S  T  N  S  R  L  C  A  V  F  V  R  D  G  Q  S  V  I  G
         .         .         .         .         .         .
AGCCTGCGCCAGCCCGTATGAAGGCAGGTACAGAGACATGTACGACGCGCTGCGGCGCCT
  A  C  A  S  P  Y  E  G  R  Y  R  D  M  Y  D  A  L  R  R  L
         .      3500         .         .         .         .
GCTGTACATGATCTATATGTCCGGCCTTGCCGTACGCGTCCACGTCAGCAAGGAAGAGCA
  L  Y  M  I  Y  M  S  G  L  A  V  R  V  H  V  S  K  E  E  Q
         .         .         .         .         .      3600
GTATTACGACTACGAGGACGCCACATTCCAGACCTATGCCCTCACCGGCATTTCCCTCTG
  Y  Y  D  Y  E  D  A  T  F  Q  T  Y  A  L  T  G  I  S  L  C
         .         .         .         .         .         .
CAACCCGGCAGCGTCGATATGCTGAGCCGCCGGCTCGGATCTGTTCGCCTGTCCATGTTT
  N  P  A  A  S  I  C  U

         .         .         .      3700         .         .
TTCCTTGACGGATACCGCGAATGAATCCCTTGAAAGACTTGAGAGCATCGCTACCGCGCC
         .         .         .         .         .         .
TGGCCTTCATGGCAGCCTGCACCCTGTTGTCCGCCACGCTGCCCGACCTCGCCCAGGCCG
         .      3800         .         .         .         .
GCGGCGGGCTGCAGCGCTGTCAACCACTTCATGGCGAGCATCGTGGTCGTACTGCCGCGG
         .         .         .         .         .      3900
CGGTCAGTGGCCACGGTGACCATCGCCATAATCTGGGCGGGCTACAAGCTGCTGTTCCGG
         .         .         .         .         .         .
CACGCCGATGTGCTGGACGTGGTGCGTGTGGTGCTGGCGGGAGCTGCTGATCGGCGCATC
         .         .         .      4000         .         .
GGCCGAAATCGCTCGTTATCTGCTGACCTGAATCCTGGACGTATCGAACATGCGTGATCC
         .<-------------         .         .         .---------.
GCTTTTCAAGGGCTGCACCCGGCGCCGCGATGCTGATGGCGTACCCGCCACGGCAGGCCG
-------->.      4100         .         .         .         .
TGTGCAGCCGGCACCATTCCCTGCTGGGCCATCTCGGTTCAGCATCCGCTTTCTGGCCTT
         .         .         .         .         .      4200
GTTTCCCGTGGCATTGCTGGCGATGCGGATCATGATCCGGCGCGATGACCAGCAGTTCCG
  Sau3A
CCT[GATC]
```

The deduced amino acid sequences of the individual subunits are shown in the single letter code below the nucleotide sequence. The proposed signal peptide cleavage sites ar indicated by asterisks. The start at the protein coding r gion for each subunit is indicated by the box and arrow v r the initiation codon. Putative ribososal binding sites ar underlined. The promotor-like sequence is shown in the −35 and −10 boxes. Proposed transcriptional start sit is indicatedby the arrow in the CAT box. Inverted repeats ar indicated by the arrows in th flanking regions.

Assignment of the Subunit Cistrons.

The DNA sequence shown in Table 2 was translated in all six reading frames and the reading frames are shown in FIG. 4 *b,c*. The open reading frame (ORF) corresponding to the S4 subunit was identified and is shown in FIG. 4*d*. The assignment of the other subunits to their respective ORFs is based on the following lines of evidence: size of ORFs, high coding probability, deduced amino acid composition, predicted molecular weights, ratios of acidic to basic amino acids, amino acid homology to other bacterial toxins, mapping of Tn5-induced mutations, and partial amino acid sequence.

Significant ORFs, long enough to code for any of the five toxin subunits, were analyzed by the statistical TESTCODE algorithm designed to differentiate between real protein coding sequences and fortuitous open reading frames in accordance with Fickett, Nucleic Acids Res. 10:5303, 1982. The amino acid composition of each ORF with a high protein coding probability was calculated, starting from either the predicted amino terminus of the mature proteins or from the first amino acid for the mature protein determined by amino acid sequencing HPLC purified subunits. These data were then compared with the experimentally-determined compositions of the individual subunits as described by Tamura et al. Biochem. 21:5516, 1982. Based on the similarity of the amino acid compositions shown in Table 3, all five subunits were identified and assigned to the ORF regions shown in FIG. 4*d*. Table 3 shows that the deduced amino acid composition from all five assigned subunits are in good agreement with the experimentally-determined compositions of Tamura et al supra, with two significant exceptions. First, the S1 subunit contains no lysine residues in the deduced amino acid sequence, whereas 2.2% lysine was experimentally determined. Second, in subunits S2, S3, S4, and S5 the proportion of cysteines are substantially underestimated in the experimentally observed compositions. These discrepancies, as well as the remaining minor differences observed for all subunits, including the previously assigned S4 subunit, can most reasonably be explained by experimental error during amino acid analysis. Similar analyses, in which a DNA-deduced amino acid composition was compared with an experimentally-derived amino acid composition show the same minor differences. The absence of lysine residues in S1 may explain why lysine-specific chemical modification does not affect the biological and enzymatic activities of S1. The amino acid composition of the ORFs (FIG. 4*b, c*) not assigned to any subunit show no similarity to any of the experimentally-determined amino acid compositions, although some of these ORFs are quite long and have a high coding potential. It is possible that these regions code for other proteins, perhaps involved in the assembly or transport of pertussin toxin.

The experimentally-estimated molecular weight and isoelectric point of the individual subunits were compared to the calculated molecular weight and ratio of acidic to basic amino acids of the putative proteins encoded by the ORFs shown in FIG. 4. As expected for this comparison, Table 3 shows that differences in the ratios reflect corresponding differences in the observed isoelectric points for each subunit, i.e., the higher the acidic content, the lower the isoelectric point. The comparison of the molecular weights also shows good correspondence to the experimentally-determined values, with slight differences for the S1 (less than 10%) and the S5 (about 15%) subunits. These small differences are within acceptable limits for protein molecular weights determined by SDS-PAGE.

TABLE 3

Comparison of the Observed Amino Acid Composition With the Calculated Composition From DNA Sequence for Mature Pertussis Toxin Subunits

| | S1 | | S2 | | S3 | | S4 | | | S5 | |
|---|---|---|---|---|---|---|---|---|---|---|---|
| | | | | | | | Observed values[a] | | | | |
| | Observed values[a] | Calculated values | Observed values[a] | Calculated values | Observed values[a] | Calculated values | Exp. 1 | Exp. 2 | Calculated values | Observed values[a] | Calculated values |
| Mr[b] | 28 k | 26.0 k | 23 k | 21.9 k | 22 k | 21.9 k | 11.7 k | — | 12.1 k | 9.3 k | 11.0 k |
| A/B[c] | — | 1.3 | — | 0.89 | — | 0.83 | — | — | 0.65 | — | 1.4 |
| pI[d] | 5.8 | — | 8.5 | — | 8.8 | — | 10.0 | 10.0 | — | 5.0 | — |
| Ala | 10.6 | 11.5 | 6.5 | 6.0 | 11.7 | 11.1 | 9.4 | 9.8 | 8.2 | 9.8 | 9.0 |
| Arg | 5.9 | 9.0 | 6.2 | 6.0 | 6.1 | 6.5 | 5.1 | 5.4 | 5.5 | 3.3 | 3.0 |
| Asn[e] | 9.3 | 5.6 | 6.3 | 2.5 | 6.3 | 2.0 | 5.3 | 5.0 | 0.9 | 8.2 | 3.0 |
| Asp | — | 4.3 | — | 4.0 | — | 4.0 | — | — | 3.6 | — | 5.0 |
| Cys | 1.0 | 0.9 | 1.3 | 3.0 | 1.1 | 3.0 | 0.9 | 0.7 | 3.6 | 1.6 | 4.0 |
| Gln[f] | 10.6 | 3.0 | 8.7 | 3.5 | 9.0 | 4.5 | 9.5 | 9.1 | 3.6 | 9.3 | 3.0 |
| Glu | — | 7.3 | — | 4.0 | — | 3.5 | — | — | 4.5 | — | 6.0 |
| Gly | 11.2 | 7.7 | 13.0 | 10.6 | 11.9 | 10.1 | 9.6 | 8.9 | 6.4 | 8.7 | 8.0 |
| His | 1.7 | 2.6 | 2.4 | 2.0 | 1.0 | 1.0 | 0.5 | 0.5 | 0.9 | 3.0 | 3.0 |
| Ile | 3.2 | 3.4 | 4.2 | 5.5 | 5.0 | 6.5 | 2.0 | 1.8 | 1.8 | 3.4 | 3.0 |
| Leu | 5.5 | 3.4 | 7.3 | 7.5 | 8.1 | 8.0 | 8.4 | 8.7 | 9.1 | 13.8 | 15.0 |
| Lys | 2.2 | 0 | 3.4 | 3.0 | 2.7 | 2.5 | 6.9 | 7.6 | 7.3 | 4.7 | 5.0 |
| Met | 1.6 | 1.7 | 1.4 | 1.5 | 1.1 | 1.5 | 5.1 | 4.3 | 7.3 | 1.6 | 2.0 |
| Phe | 3.5 | 3.0 | 3.2 | 2.5 | 3.2 | 2.5 | 3.6 | 4.5 | 4.5 | 4.9 | 5.0 |
| Pro | 4.4 | 3.4 | 4.6 | 4.5 | 5.7 | 5.0 | 9.1 | 9.9 | 10.0 | 5.6 | 5.0 |
| Ser | 10.6 | 9.8 | 8.5 | 8.5 | 6.3 | 5.0 | 8.0 | 7.3 | 5.5 | 6.9 | 6.0 |
| Thr | 7.4 | 7.3 | 10.4 | 10.1 | 8.2 | 8.0 | 5.0 | 5.1 | 4.5 | 6.9 | 7.0 |
| Trp | ND[g] | 0.9 | ND | 1.0 | ND | 0.5 | ND | ND | 0 | ND | 1.0 |
| Tyr | 4.6 | 8.1 | 7.6 | 8.0 | 7.9 | 9.5 | 2.2 | 2.0 | 1.8 | 4.3 | 4.0 |
| Val | 6.7 | 7.3 | 4.9 | 6.0 | 4.7 | 5.0 | 9.4 | 9.4 | 10.9 | 4.0 | 3.0 |

[a]Data from Tamara et.al. Biochem 21:5516, 1982.
[b]Mr = molecular weight.
[c]A/B = acid amino acids (Glu + Asp) ÷ basic amino acids (Arg + Lys).
[d]pI = is electric pH.
[e]Observed values are Asn + Asp.
[f]Observed values are Gln + Glu.

TABLE 4

Comparison of Two Homologous Regions in ADP-ribosylating subunits of *Pertussis*, *Cholera*, and *E. coli* Heat Labile Toxins.

Region 1

| | |
|---|---|
| *Pertussis* S1 subunit | (8) Tyr Arg Tyr Asp Ser Arg Pro Pro (15) |
| *Cholera*[a] A subunit | (6) Tyr Arg Ala Asp Ser Arg Pro Pro (13) |
| *E. coli*[a] HLT A subunit | (6) Tyr Arg Ala Asp Ser Arg Pro Pro (13) |

TABLE 4-continued

Comparison of Two Homologous Regions in ADP-ribosylating subunits of *Pertussis*, *Cholera*, and *E. coli* Heat Labile Toxins.

Region 2

| | | |
|---|---|---|
| *Pertussis* S1 subunit | (51) Val Ser Thr Ser Ser Ser Arg Arg (58) |
| *Cholera*[a] A subunit | (60) Val Ser Thr Ser Ile Ser Leu Arg (67) |
| *E. coli*[a] HLT A subunit | (60) Val Ser Thr Ser Leu Ser Leu Arg (67) |

The numbers in parentheses refer to the amino acid position in the mature proteins.
[a]Data from Yamamoto et al, FEBS Letter, 169: 241, 1983.
HLT = Heat labile Toxin Comparison of Codon Usage Between Pertussis Toxin and Strongly and Weakly Expressed *E. coli* Genes

| | | Pertussis Toxin[a] | | | | | | *E. coli*[b] | | | | Pertussis Toxin[a] | | | | | | *E. coli*[b] | |
|---|---|---|---|---|---|---|---|---|---|---|---|---|---|---|---|---|---|---|---|
| | | S1 | S2 | S3 | S4 | S5 | PTX[c] | S[c] | W[c] | | | S1 | S2 | S3 | S4 | S5 | PTX[c] | S[c] | W[c] |
| Ala | GCU | 3 | 0 | 1 | 0 | 1 | 5 | 33 | 17 | Lys | AAA | 0 | 2 | 0 | 1 | 1 | 4 | 49 | 31 |
| | GCC | 17 | 7 | 14 | 9 | 4 | 52 | 9 | 34 | | AAG | 0 | 5 | 7 | 7 | 4 | 24 | 20 | 8 |
| | GCA | 5 | 3 | 2 | 1 | 1 | 12 | 23 | 20 | Met | AUG | 4 | 3 | 4 | 9 | 2 | 22 | 27 | 25 |
| | GCG | 9 | 5 | 8 | 5 | 5 | 33 | 25 | 28 | Phe | UUU | 0 | 1 | 0 | 1 | 1 | 3 | 7 | 29 |
| Arg | CGU | 3 | 2 | 0 | 1 | 0 | 6 | 42 | 19 | | UUC | 7 | 4 | 5 | 4 | 4 | 25 | 22 | 19 |
| | CGC | 12 | 7 | 9 | 4 | 0 | 33 | 19 | 25 | Pro | CCU | 1 | 1 | 0 | 1 | 0 | 3 | 4 | 6 |
| | CGA | 1 | 0 | 0 | 0 | 0 | 1 | 1 | 5 | | CCC | 5 | 3 | 2 | 6 | 1 | 17 | 0.4 | 9 |
| | CGG | 5 | 3 | 1 | 2 | 2 | 13 | 0.2 | 8 | | CCA | 0 | 1 | 2 | 0 | 0 | 3 | 5 | 9 |
| | AGA | 1 | 1 | 1 | 0 | 1 | 4 | 1 | 5 | | CCG | 4 | 6 | 7 | 5 | 5 | 28 | 31 | 19 |
| | AGG | 3 | 1 | 3 | 0 | 0 | 7 | 0.2 | 3 | Ser | UCU | 0 | 1 | 0 | 0 | 0 | 1 | 18 | 7 |
| Asn | AAU | 4 | 2 | 0 | 1 | 1 | 8 | 2 | 19 | | UCC | 7 | 6 | 3 | 2 | 4 | 23 | 17 | 9 |
| | AAC | 9 | 3 | 6 | 0 | 2 | 20 | 30 | 19 | | UCA | 0 | 2 | 0 | 0 | 0 | 2 | 1 | 7 |
| Asp | GAU | 2 | 3 | 1 | 2 | 1 | 9 | 22 | 35 | | UCG | 5 | 0 | 2 | 0 | 2 | 9 | 2 | 12 |
| | GAC | 8 | 6 | 7 | 2 | 5 | 29 | 39 | 20 | | AGU | 0 | 0 | 0 | 1 | 0 | 1 | 2 | 11 |
| Cys | UGU | 0 | 0 | 0 | 0 | 0 | 0 | 2 | 6 | | AGC | 12 | 10 | 5 | 5 | 3 | 36 | 9 | 12 |
| | UGC | 3 | 7 | 6 | 4 | 4 | 25 | 4 | 7 | Thr | ACU | 4 | 2 | 1 | 1 | 2 | 10 | 20 | 9 |
| Gln | CAA | 1 | 2 | 3 | 3 | 0 | 9 | 7 | 17 | | ACC | 10 | 9 | 8 | 3 | 4 | 35 | 26 | 23 |
| | CAG | 7 | 5 | 7 | 1 | 3 | 24 | 32 | 32 | | ACA | 3 | 1 | 1 | 0 | 0 | 5 | 3 | 6 |
| Glu | GAA | 10 | 5 | 5 | 5 | 3 | 29 | 63 | 40 | | ACG | 6 | 9 | 7 | 2 | 2 | 27 | 5 | 15 |
| | GAG | 7 | 3 | 2 | 0 | 3 | 15 | 20 | 19 | Trp | UGG | 5 | 2 | 1 | 1 | 1 | 10 | 5 | 13 |
| Gly | GGU | 1 | 1 | 2 | 1 | 0 | 5 | 43 | 24 | Tyr | UAU | 8 | 6 | 8 | 2 | 3 | 28 | 6 | 18 |
| | GGC | 15 | 16 | 13 | 7 | 7 | 59 | 33 | 27 | | UAC | 11 | 10 | 11 | 0 | 2 | 35 | 19 | 12 |
| | GGA | 3 | 4 | 3 | 0 | 2 | 12 | 1 | 8 | Val | GUU | 2 | 1 | 1 | 1 | 0 | 5 | 37 | 21 |
| | GGG | 0 | 1 | 3 | 0 | 0 | 4 | 3 | 13 | | GUC | 10 | 7 | 6 | 6 | 3 | 33 | 8 | 13 |
| His | CAU | 3 | 4 | 1 | 1 | 2 | 11 | 4 | 18 | | GUA | 3 | 1 | 2 | 1 | 0 | 7 | 23 | 9 |
| | CAC | 3 | 2 | 3 | 1 | 2 | 11 | 14 | 11 | | GUG | 4 | 5 | 2 | 4 | 2 | 17 | 16 | 24 |
| Ile | AUU | 3 | 3 | 3 | 0 | 0 | 9 | 13 | 30 | End | UAA | — | — | — | — | — | 0 | ND[d] | ND |
| | AUC | 7 | 8 | 9 | 2 | 4 | 31 | 15 | 23 | | UAG | 1 | — | — | — | — | 1 | ND | ND |
| | AUA | 0 | 1 | 4 | 0 | 2 | 7 | 0.4 | 5 | | UGA | — | 1 | 1 | 1 | 1 | 4 | ND | ND |
| Leu | UUA | 0 | 1 | 0 | 0 | 0 | 1 | 2 | 14 | fMet | AUG | 1 | 1 | 1 | — | 1 | 4 | ND | ND |
| | UUG | 1 | 2 | 3 | 2 | 3 | 11 | 3 | 12 | | GUG | — | — | — | 1 | — | 1 | ND | ND |
| | CUU | 1 | 2 | 2 | 1 | 1 | 7 | 5 | 14 | | | | | | | | | | |
| | CUC | 4 | 7 | 5 | 3 | 4 | 24 | 6 | 13 | | | | | | | | | | |
| | CUA | 0 | 1 | 0 | 0 | 0 | 1 | 1 | 4 | | | | | | | | | | |
| | CUG | 5 | 9 | 14 | 9 | 10 | 48 | 66 | 56 | | | | | | | | | | |

[a]Absolute codon usage for the subunit cistrons include the signal peptides (Table 2). The number of codons in the five individual subunits are 269(S1), 227(S2), 228(S3), 132(S4), and 121(S5).
[b]Data deduced from Grosjean and Fiers reference 32. S = strongly expressed genes; W = moderately to weakly expressed genes.
[c]Relative codon usage per 1000 codons. Pertussis usage based on 977 codons for the pertussis toxin gene (PTX). *E. coli* usage based on 5253 codons for highly expressed genes (8) and 5231 codons for moderate to weakly expressed genes (W).
[d]ND = not determined.

Figure 4D:
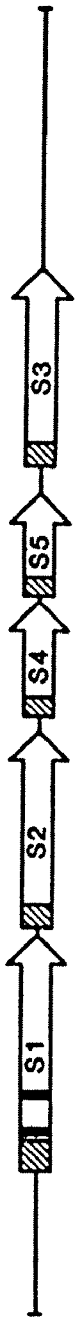
Figures 5A, 5B, 5C, 5D:
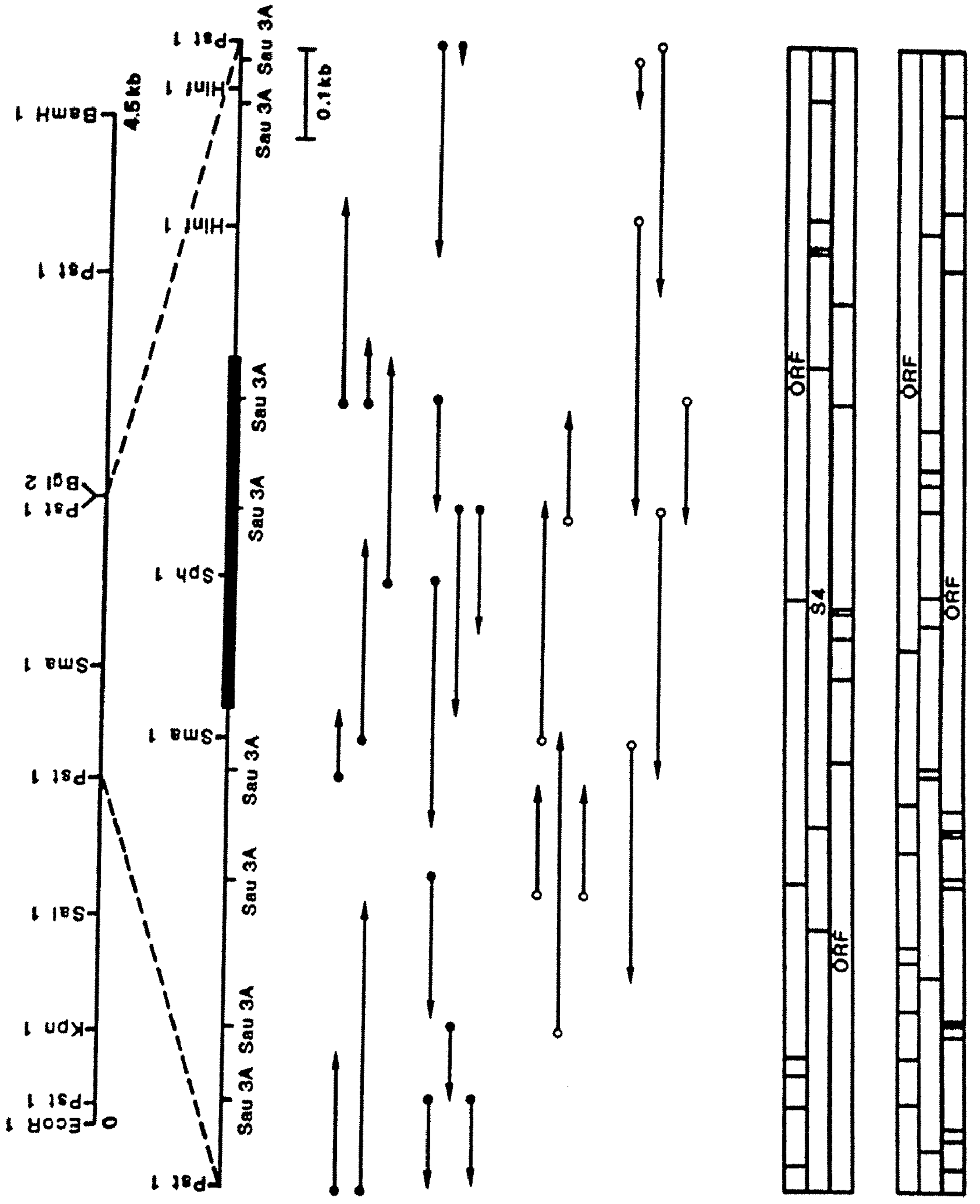
FIG. 5 shows the physical map of the pertussis toxin S4 subunit gene. a) Restriction map of the 4.5 kilobase pair (kb) EcoRI/BamHI fragment inserted into pMC1403. b) Detailed restriction map and sequencing strategy of the PstI fragment B containing the S4 subunit gene. Only the restriction sites used for subcloning prior to sequencing are shown. Closed circle arrow shows the sequencing using dideoxy chain termination and open circled arrows show the sequencing strategy using base-specific chemical cleavage. The arrows show the direction and the length of the sequence determination. The heavy black line represents the S4 coding region. c) Open reading frames in the three forward directions. d) Open reading frames in the three backward directions. The vertical lines indicate termination codons.

The assignment for S1 in the location shown in FIG. 4*d* is further supported by a significant homology of two regions in the S1 amino acid sequence with two related regions in the A subunits of both cholera and *E. coli* heat labile toxins. These homologous regions, shown in Table 4, may be part of functional domains for a catalytic activity in the subunits for all three toxins. Furthermore, the assignment for S1, as well as the correct prediction of the signal peptide cleavage site, is supported by preliminary amino acid sequence data for the mature protein (unpublished results).

Subunits S2 and S3 share 70% amino acid homology, which makes the correct assignment of these subunits to their ORFs difficult if it is based only on the amino acid composition and the molecular weight. Nevertheless, the gene order could be determined as shown in FIG. 4*d* based on the location of a Tn5-induced mutation responsible for the lack of active pertussis toxin in the supernatant of the mutant *B. pertussis* strains. This Tn5 insertion was mapped 1.3 kb downstream of the start site for the S4 subunit gene, as indicated by the arrow in FIG. 4*a*. As can be seen in FIG. 4, the Tn5-insertion in those mutants would be located in the ORF for S3. Although unable to produce active pertussis toxin, the mutants are still able to produce the S2 subunit. Thus, the Tn5-insertion in those mutants is not located in the structural gene for S2. Therefore, the ORFs for S2 and S3 could be differentiated.

Amino Acid Sequences.

The amino acid sequence for each subunit was deduced from the nucleotide sequence and is shown in Table 2. The mature proteins contain 234 amino acids for S1 (SEQ ID NO: 6), 199 amino acids for S2 (SEQ ID NO: 7), 110 amino acids for 84 (SEQ ID NO: 8), 100 amino acids for S5 (SEQ ID NO: 9) and 199 amino acids for S3 (SEQ ID NO: 10), in the order of the gene arrangement from the 5-end to the 3-end. Most likely all subunits contain signal peptides, as expected for secretory proteins. The length of the putative signal peptides was estimated after the analyses of the hydrophobicity plot, the predicted secondary structure and application of von Heijne's rule for the prediction of the most probable signal peptide cleavage site. The cleavage site for each subunit is shown in Table 2 by the asterisks. The correct prediction of the cleavage sites for S4 and S1 (unpublished) was confirmed by amino terminal sequencing of the purified mature subunits. The length of the signal peptides varies from 34 residues for S1, 28 residues for S3, and 27 residues for S2, to 21 residues for S4, and 20 residues for S5. All of the signal peptides contain a positively-charged amino terminal region of variable length, followed by a sequence of hydrophobic amino acids, usually in-helical or partially-helical, partially-pleated conformation. A less hydrophobic carboxy-terminal region follows, usually ending in-turn conformation at the signal peptide cleavage site. All subunits except S5 follow the −1, −3, rule, which positions the cleavage site after Ala-X-Ala. The amino-terminal charge for the subunit signal peptides varies between +4 for S1 and +1 for S4 and S5. All described properties correspond very well to the general properties for bacterial signal peptides.

Two different initiation codons are used for the translation of all subunits in *B. pertussis*, i.e., the most frequently used ATG for S1, S2, S3 and S5, and the less frequently used GTG for S4. The codon usage (Table 4) is unsuitable for efficient translation of the pertussis toxin gene in *E. coli*. This is reflected by the codon choice for frequently used amino acids, such as alanine, arginine, glycine, histidine, lysine, proline, serine and valine. Whether pertussis toxin is a strongly or weakly expressed protein in *B. pertussis* and whether this expression is regulated by the presence of a precise relative amount of the different tRNA isoacceptors, possibly different from *E. coli*, remains to be established. This can be evaluated by in vitro translation using *E. coli* and *B. pertussis* cell free extracts.

Closer examination of the amino acid sequence reveals the striking absence of lysines in S1. Another interesting feature is the overall relatively high amount of cysteines as compared to *E. coli* proteins. Cysteines do not seem to be involved in inter-subunit links to construct the quaternary structure of the toxin, since all subunits can be easily separated by SDS-PAGE in the absence of reducing agents. Most likely, the cysteines are involved in intrachain bonds, since reducing agents significantly change the electrophoretic mobility of all subunits but S4. Serines, threonines and tyrosines also are represented more frequently than in average *E. coli* proteins. The hydroxyl groups of these residues may be involved in the quaternary structure through hydrogen bonding.

Analysis of the Flanking Regions.

Since all pertussis toxin subunits are closely linked and probably expressed in a very precise ratio, it is possible that they are arranged in a polycistronic operon. A polycistronic arrangement for the subunit cistrons also has been described for other bacterial toxins bearing similar enzymatic functions, such as diphtheria cholera and *E. coli* heat labile toxins. Therefore, the flanking regions were analyzed for the presence of transcriptional signals. In the 5' flanking region, starting at position 469, the sequence TAAAATA was found, which six of the seven nucleotides found in the ideal TATAATA Pribnow or −10 box. An identical sequence can be found in several other bacterial promoters, including the lambda L57 promoter. Given the fact that most transcripts start as a purine residue about 5-7 nucleotides downstream from the Pribnow box, the transcriptional start site was tentatively located at the adenine residue at position 482. This residue is located in the sequence CAT, often found at transcriptional start sites. Upstream from the proposed −10 box, the sequence CTGACC starts at position 442. This sequence matches four of the six nucleotides found in the ideal *E. coli* −35 box TTGACA. The mismatching nucleotides in the proposed pertussis toxin −35 box are the two end nucleotides, of which the 3' residue is the less important nucleotide in the *E. coli* −35 consensus box. A replacement of the T by a C in the first position of the consensus sequence can also be found in several *E. coli* promoters. The distance between the two proposed promoter boxes is 21 nucleotides, a distance of the same length has been found in the galP1 promotor and in several plasmid promoters. The proposed −35 box is immediately preceded by two overlapping short inverted repeats with calculated free energies of −15.6 kcal and −8.6 kcal, respectively. Inverted repeats can also be found at the 5'-end of the cholera toxin promotor. In both cases, they may be involved in positive regulation of the toxin promoters. None of the ORFs assigned to the other subunit is closely preceded by a similar promoter-like structure. However, a different promoter-like structure was found associated with the S4 subunit ORF.

The 3'-flanking region has been examined for the presence of possible transcriptional termination sites. Several inverted repeats could be found; the most significant is located in the region extending from position 4031 to 4089 and has a calculated free energy of −41.4 kcal. None of the inverted repeats are immediately followed by an oligo(dT) stretch, which may suggest that they function in a rho-dependent fashion. Preliminary experiments indicate, however, that neither inverted repeat functions efficiently in *E. coli* (results not shown). Whether they are functional in *B. pertussis* remains to be established and can be investigated by a small deletion or site-directed mutagenesis experiments, which are feasible now that the DNA sequence is known. Another possibility is that the five different subunits may not be the only proteins encoded in the polycistronic operon and that cistrons for other peptides, possibly involved in regulation, assembly or transport, are cotranscribed. Non-structural proteins involved in the posttranslational processing of *E. coli* heat labile toxin have been proposed. However, no significantly long ORF was found at the 3'-end of the nucleotide sequence shown in FIG. 4*b*. If other proteins are encoded by the same polycistronic operon, their coding regions must be located further downstream.

Additionally, the 5'-flanking region of each cistron was also examined for the presence of ribosomal binding sites. Neither the ribosomal binding sequences for *B. pertussis* genes, nor the 3'-end sequence of the 16S rRNA are known. Therefore, the flanking regions could be compared with only the ribosomal binding sequences of heterologous procaryotic organisms represented by the Shine-Dalgarno sequence. Preceding the S1 initiation codon, the sequence GGGGAAG was found starting at position 495. This sequence shares four out of seven nucleotides with ideal Shine-Dalgarno sequence AAGGAGG. The two first mismatching nucleotides in the pertussis toxin gene would not destabilize the hybridization to the 3'-end of the *E. coli* 16 S rRNA. This putative ribosomal binding site is close enough to the initiation codon for S1 to be functional in *E. coli*. Another possible Shine-Dalgarno sequence overlaps the first one and also matches four out of seven nucleotides to the consensus sequence. The mismatching nucleotides, however, have a more destabilizing effect than the ones found in the first sequence. The S2 subunit ORF is not closely preceded by a ribosomal binding sequence, which may suggest that S2 is translated through a mechanism not involving the detachment and reattachment of the ribosome between the coding regions for S1 and S2. The short distance between the S1 and S2 cistrons, and the absence of a ribosomal binding site are characteristic of this mechanism. A ribosomal binding site for S4 in the sequence CAGGGCGGC, starting at position 2066 is possible. The ORF for S5 is preceded by the sequence AAGGCG, starting at position 2485, which matches five out of six nucleotides in the consensus sequence AAGGAG. Finally, S3 is preceded by the sequence GGGAACAC, which is very similar to the proposed ribosomal binding site for S1, i.e., GGGAAGAC.

Taken as a whole, the results described herein clearly establish the complete nucleotide sequence of all structural cistrons for pertussis toxin. The gene order, as shown in FIG. 4, is S1, S2, S4, S5, and S3. The calculated molecular weights from the deduced sequence of the mature peptides are 26,024 for S1; 21,924 for S2; 12,058 for S4; 11,013 for S5 and 21,873 for S3. Since S4 is present in two copies per toxin molecule, the total molecular weight for the holotoxin is about 104950. This is in agreement with the apparent molecular weight estimated by non-denaturing PAGE. The most striking feature of the predicted peptide sequences is the high homology between S2 and S3. The two peptides share 70% amino acid homology and 75% nucleotide homology. This suggests that both cistrons were generated through a duplication of an ancestral cistron followed by mutations which result in functionally-different peptides. The differences between S2 and S3 are scattered throughout the whole sequence and are slightly more frequent in the amino-terminal half of the peptides. Despite their high homology, also reflected in the predicted secondary structures and hydrophilicities, S2 and S3 subunits cannot substitute for each other in the functionally-active pertussis toxin. The comparison between the two subunits may be useful in localizing their functional domains in relation to their primary, secondary and tertiary structure. On the basis of the differences, S2 and S3 are divided into two domains, the amino-terminal and the carboxy-terminal. Each of the subunits binds to a S4 subunit. This function could be located in the more conserved carboxyl-terminal domains of S2 and S3. The two resulting dimers are thought to bind to one S5 subunit. This function could be assigned to the more divergent amino-terminal domains of S2 and S3. Alternatively, it is possible that the dimers bind to the S3 subunit through S4 and that the amino-terminal domains of S2 and S3 are involved in some other function, possibly the interaction of the binding moiety (S2 through S5) with the enzymatically-active moiety (S1).

The enzymatically-active S1 subunit was compared to the A subunits of other bacterial toxins. Two regions with significant homology to cholera and *E. coli* heat labile toxins were found (Table 4). They are tandemly located in analogous regions of all three toxins. However, the three amino acid differences found in these regions cannot be explained by single base pair changes in the DNA. Furthermore, in most cases the homologous amino acids use quite different codons in pertussis toxin compared to cholera and *E. coli* heat labile toxins. This, together with the fact that no other significant homology in the primary structure could be found and that the amino acid sequences of the other subunits are completely different from the sequence of any other ADP-ribosylating toxin, strongly suggests that pertussis toxin is not evolutionarily related to any of the other known bacterial toxins. The limited homology of S1 subunit to the A subunits of cholera and *E coli* heat labile toxins could be due to convergent evolution, since all three toxins contain a very similar enzymatic activity and use a relatively closely-related acceptor substrate (Ni protein for pertussis toxin and Ns protein for cholera and *E. coli* heat labile toxins). The NAD-binding site for the two enterotoxins has been identified at the carboxy-terminal region of their A1 subunit. No significant homology could be found between the carboxy-terminus of the enterotoxins, nor any other NAD-binding enzymes, and the analogous region in the S1 subunit. This suggests that the NAD-binding function of the ADP-ribosylating enzymes is dependent more on the secondary or tertiary structures, than on the primary structures. It is proposed that the two enzymatically-active domains lie in different regions of the protein, one at the amino-terminal half of the subunit for the acceptor substrate (Ni) binding and the other at the carboxy-terminal half of the subunit for the donor substrate (NAD+) binding.

The presence of a promoter-like structure upstream of the S1 subunit cistron and possible transcriptional termination signals downstream of the S3 subunit cistron suggests that pertussis toxin, like many other bacterial toxins, is expressed through a polycistronic mRNA. The inverted repeats immediately preceding the proposed promoter may be sites for positive regulation of expression of the toxin in *B. pertussis*. Evidence for a positive regulation came through the discovery of the vir gene, the product of which is essential for the production of many virulence factors, including pertussis toxin. Recent evidence in our laboratory suggests that the proposed inverted repeats in the 3' flanking region are not very efficient in transcriptional termination in *E. coli* (results not shown). The termination of transcription in *B. pertussis* may be carried out by a slightly different mechanism than in *E. coli*; on the other hand, the polycistron may contain other, not yet identified, genes related to expression of functionally-active pertussis toxin or other virulence factors. We have described a promoter-like structure preceding subunit S4 and possible termination signals following the S4 cistron. The S4 promoter-like structure is quite different from the proposed promoter at the beginning of S1 subunit. It is part of an inverted repeat, suggesting an iron regulation of the S4 subunit expression. This is supported by the fact that chelating agents stimulate the accumulation of active pertussis toxin in cell supernatants. It is thus possible that pertussis toxin is expressed efficiently by two dissimilar promoters, one (promoter 1) located in the 5'-flanking region and the other (promoter 2) located upstream of S4. Both promoters would be regulated by different mechanisms. Promoter 1 would be positively regulated, possibly by the vir gene product, and promoter 2 would be negatively regulated by the presence of iron. In optimal expression conditions, such as in the presence of the vir gene product and in the absence of iron, the S4 subunit cistron would be transcribed twice for every transcription of the other subunits. This is a mechanism that would explain the stoichiometry of the pertussis toxin subunits of 1:1:1:2:1 for S1:S2:S3:S4:S5, respectively, in the biologically active holotoxin.

Attempts to express the pertussis toxin gene in *E. coli* have been heretofore unsuccessful, although very sensitive monoclonal and polyclonal antibodies are available. This lack of expression of *E. coli* may reside in the fact that *B. pertussis* promoters are not efficiently recognized by the *E. coli* RNA polymerase. Analysis of the promoter-like structures of the pertussis toxin gene and their comparison to strong *E. coli* promoters show very significant differences, indeed, of which the most striking ones are the unusual distances between the proposed −35 and −10 boxes in the pertussis toxin promoters. The distance between those two boxes in strong *E. coli* promoters is around 17 nucleotides, whereas the distances in the two putative pertussis toxin promoters are 21 nucleotides for the S4 subunit promoter. Preliminary results in our laboratory using expression vectors designed to detect heterologous expression signals which are able to function in *E. coli* further indicate that *B. pertussis* promoters may not be recognized by the *E. coli* expression machinery. In addition, the codon usage for pertussis toxin is extremely inefficient for translation in *E. coli* (Table 5). Preliminary experiments show that the insertion of a fused lac/trp promoter in the KpnI site upstream of the pertussis toxin operon probably enhances transcription but does not produce detectable levels of pertussis toxin (unpublished results). Efficient expression in *E. coli* would require resynthesis of the pertussis toxin operon, respecting the optimal codon usage for expression in *B. pertussis*, since no other *B. pertussis* gene has heretofore been sequenced.

The cloned and sequenced pertussis toxin genes are useful for the development of an efficient and safer vaccine against whooping cough. By comparison to other toxin genes with similar biochemical functions are by physical identification of the active sites either for the ADP-ribosylation in the S1 subunit or the target cell binding in subunits S2 through S4. It is now possible to modify those sites by site-directed mutagenesis of the *B. pertussis* genome. These modifications could abolish the pathobiological activities of pertussis toxin without hampering its immunogenicity and protectivity. Alternatively, knowing the DNA sequence, mapping of eventual protective epitope is now made possible. Synthetic oligopeptide comprising those epitopes will also be useful in the development of a new generation vaccine.

EXAMPLE 1

The region containing amino acid residues 8 through 15 of the S1 without (called "homology box") was chosen for site-directed mutagenesis which was accomplished by employing standard methodologies well known in the art. The specific codon changes and the resultant amino acid alterations are shown in Table 6.

To effect the mutagenic alterations, oligonucleotides [Beucage et al. *Tetrahedron Lett* 22, 1859, (1981)] were synthesized that incorporated a series of single-codon and double-codon substitution mutations within the homology box: in addition, a mutation was also designed that allowed for selective deletion of the homology region. Two previously described S1 expression vectors were used for construction of plasmids mutated in the homology box: pPTXS1/6A and pPTXS1/33B [Cieplak et al., *Proc. Natl. Acad. Sci. U.S.A.* 85, 4667 (1988)]. S1/6A is an S1 analog in which the mature amino-terminal aspartyl-aspartate is replaced with methionylvaline. Both enzymatic activity and mAb 1B7 reactivity are retained in S1/6A, whereas S1/33B has neither (Cieplak, supra). The expression vector for each S1 substitution mutant was constructed in a three-way ligation using the appropriate oligonucleotide with Acc I and Bsp MII cohesive ends, an 1824-bp DNA fragment from pPTXS1/6A (Acc I-SstI), and a 3.56-kb DNA fragment from p.TXS1/33B (Bsp MII-Sst II). The ligation and the relatively short length of the oligonucleotides required for the substitution was facilitated by the presence of novel Bsp MII and N1a IV restriction sites generated in the original construction of pPTXS1/33B. Deletion of the homology box involved ligation of mung bean nuclease-blunted Acc I site to the left of the box in pPTXS1/6A, and an N1a IV site to the right of the box in S1/33B: this ligation resulted in the excision of codons for $Tyr^8$ through $Pro^{15}$. Vector construction and retention of the altered sites were confirmed by standard restriction analysis and partial DNA sequence analysis.

Figure 6:
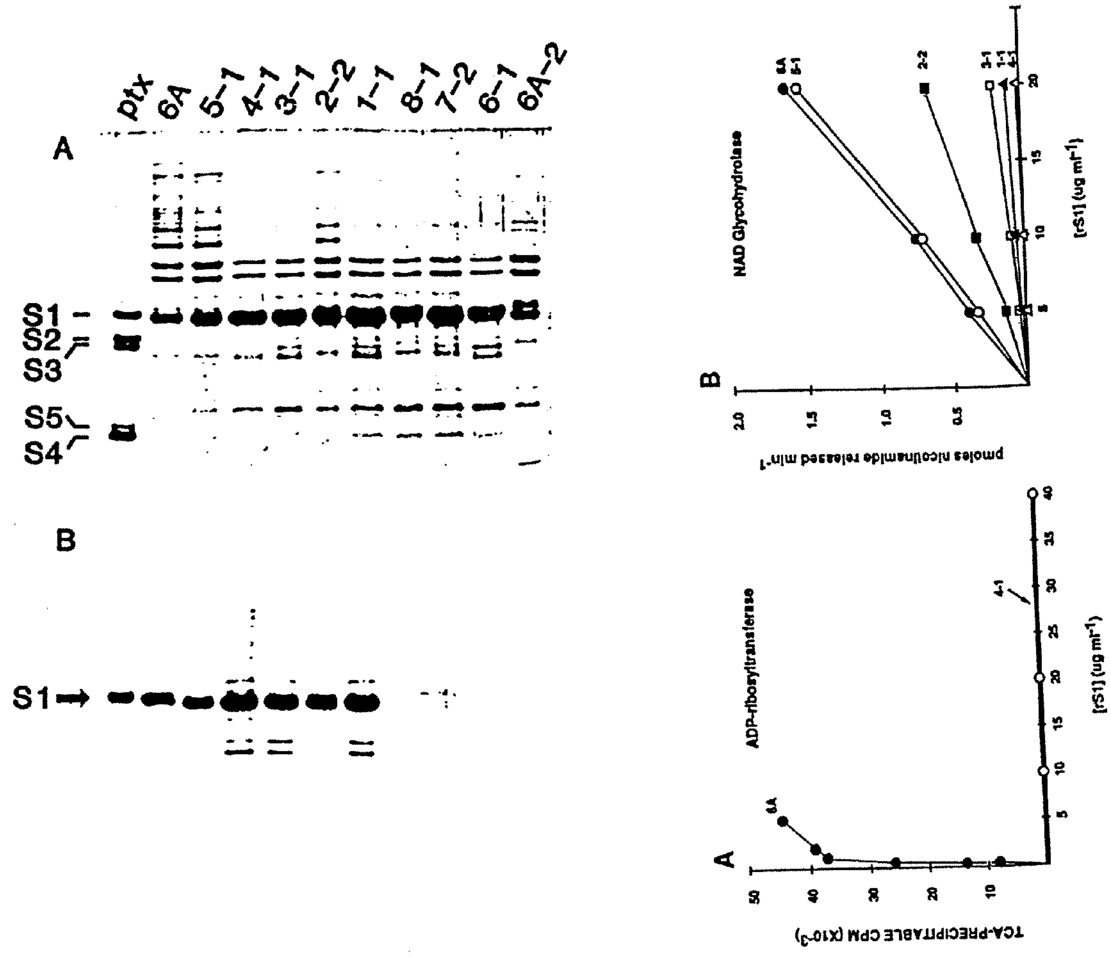

The expression vector constructions were transformed into *E. coli* and the mutant S1 genes were expressed after temperature induction. In this expression system [Burnette et al. *Bio/Technology* 6, 699 (1988)], the recombinant S1 polypeptides are synthesized at high phenotypic levels (7 to 22% of total cell protein) and aggregated into intracellular inclusions. Inclusion bodies were recovered after cell lysis (Burnette, supra) and examined by SDS-polyacrylamide gel electrophoresis (PAGE) [U. K. Laemmli, *Nature* 227, 680 (1970)] (FIG. 6A). The electrophoresis profile revealed that the mutagenized S1 products constituted the predominant protein species in each preparation and that their mobilities were very similar to that of the present S1/6A subunit.

To examine the phenotypic effects of the mutations on antigenicity, the mutant S1 polypeptides were assayed for their ability to react with the protective mAb 1B7 in an immunoblot format. The parent construction 6A (Table 6) and each of the single-codon substitution mutants (5-1, 4-1, 3-1, 2-2 and 1-1) retained reactivity with mAb 1B7 (FIG. 6B). In contrast, the reactivity of those mutants containing double-residue substitutions (8-1, 7-2, and 6-1), as well as the mutant in which the homology box had been deleted (6A-1), was significantly diminished or abolished.

The mutant S1 molecules were assayed for ADP-ribosyltransferase activity by measuring the transfer of radiolabeled ADP-ribose from [adenylate-**P]NAD to purified bovine transducing [Watkins et al. *J. Biol. Chem.*, 259, 1378 (1984): Manning et al. ibid. p. 749], a guanine nucleotide-binding regulatory protein found in the rod outer segment membranes [Stryer et al. *Annu. Rev. Cell Biol.* 2. 391 (1986)]. As shown in Table 6, each of the substitutions appeared to reduce specific ADP-ribosyltransferase activity, with the exception of mutants 5-1 and 2-2, which retained the full activity associated with the parent 6A species: 6A has approximately 60% of the ADP-ribosyltransferase activity of authentic S1 (Cieplak, supra). Neither mutant 4-1 nor any of the double-substitution mutants exhibited any significant transferase activity when compared to the inclusion body protein control (denoted 20A): this control is a polypeptide of Mr-21,678, derived from a major alternative open reading frame (orf) in the S1 gene and does not contain S1 subunit-related sequences.

The most noteworthy S1 analog produced was 4-1 ($Arg^9$-Lys). It alone among the single-substitution mutants exhibited little or no transferase activity under the conditions used (Table 6); however, unlike the double mutants, it retained reactivity with neutralizing mAb 1B7.

The results presented herein clearly demonstrate the importance and magnitude of the critical effect exerted by substitution of Arg on the enzymatic mechanisms of the S1 subunit. It is noteworthy in this report that when the Arg-Lys mutation was introduced into full-length recombinant S1, it was found that transferase activity was reduced by a factor of approximately 1000. This result establishes that the substitution at residue 9 is alone sufficient to attain the striking loss in enzyme activity and that the coincidental replacement of the two amino-terminal asparate residues in the mature S1 sequence with the Met-Val dipeptide that occurs in S1/6A is not required to achieve this reduction.

In summary, a mutant gene directing the synthesis of a mutant PTX polypeptide containing the protective epitope, but with substantially reduced enzyme activity has been produced. A safe vaccine against pertussis, in accordance with the present invention, is produced by a composition comprising immunogenic amount of the mutant PTX polypeptide in a pharmaceutically acceptable carrier. The term "substantially reduced" enzyme activity as used herein means more than about 1000 fold less enzymatic activity or almost negligible enzyme activity compared to the normal (wild type) activity.

It is understood that the examples and embodiments described herein are for illustrative purposes only and that various modifications or changes in light hereof will be suggested to persons skilled in the art and to be included within the spirit and purview of this application and the scope of the appended claims.

TABLE 6

ADP-ribosyltransferase activity of recombinant S1 mutant polypeptides. Intracellular inclusions containing the recombinant subunits produced in *E. coli* were recovered by differential centrifugation and extracted with 8M urea (18). The urea extracts were adjusted to a total protein concentration of 0.6 mg/ml, dialyzed against 50 mM tris-HCl (pH 8.0), and then centrifuged at 14,000 g for 30 min. The amount of recombinant product in the supernatant fractions was determined by quantitative densitometric scanning of proteins separated by SDS-PAGE and stained with Coomassie blue. ADP-ribosyltransferase activity was determined (17) with the use of 4.0 μg of purified bovine transducin and 100 ng of each S1 analog. The values represent the transfer of [$^{32}$P]ADP-ribose to the α subunit of transducin, as measured by total trichloroacetic acid-precipitable radioactivity, and each is given as the mean of triplicate determinations with standard deviation. The 20A product represents a negative control because its synthesis results in the formation of intracellular inclusions that lack S1-related proteins.

| Mutant designation | Amino acid change | Codon change | ADP-ribosyltransferase activity (cpm) |
|---|---|---|---|
| 6A | None | None | 23,450 ± 950 |
| 5-1 | $Tyr^8$ →Phe | TAC→TTC | 26,361 ± 1,321 |
| 4-1 | $Arg^9$ →Lys | CGC→AAG | 754 ± 7 |
| 3-1 | $Asp^{11}$→Glu | GAC→GAA | 13,549 ± 1,596 |
| 2-2 | $Ser^{12}$→Gly | TCC→GGC | 22,319 ± 2,096 |
| 1-1 | $Arg^{13}$→Lys | CGC→AAG | 7,393 ± 1,367 |
| 8-1 | $Tyr^8$ →Leu | TAC→TTG | 926 ± 205 |
| | $Arg^9$ →Glu | CGC→GAA | |
| 7-2 | $Arg^9$ →Asn | CGC→AAC | 753 ± 30 |
| | $Ser^{12}$→Gly | TCC→GGC | |
| 6-1 | $Asp^{11}$→Pro | GAC→CCG | 764 ± 120 |
| | $Pro^{14}$→Asp | CCG→GAC | |
| 20A | Alternate S1 orf | — | 839 ± 68 |

What is claimed is:

1. An isolated polypeptide comprising, an S1 subunit mutant of *B. pertussis* toxin, having reduced ADP ribosyltransferase activity as compared to wild type *B. pertussis* toxin, said polypeptide also having an epitope reactive with protective antibody against *B. pertussis* toxin, wherein said mutant consists of a mutation at amino acid position 9 of mature S1 subunit of SEQ ID NO: 6 shown in Table 2.

* * * * *